United States Patent
Douglas et al.

(10) Patent No.: US 11,337,670 B1
(45) Date of Patent: May 24, 2022

(54) METHOD AND APPARATUS FOR IMPROVING CLASSIFICATION OF AN OBJECT WITHIN A SCANNED VOLUME

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

(73) Assignee: RED PACS, LLC, Winter Park, FL (US)

( * ) Notice: Subject to any disclaimer, the term of this patent is extended or adjusted under 35 U.S.C. 154(b) by 0 days.

(21) Appl. No.: 17/340,023

(22) Filed: Jun. 6, 2021

Related U.S. Application Data

(63) Continuation of application No. 16/752,691, filed on Jan. 26, 2020, now Pat. No. 11,051,782, which is a continuation-in-part of application No. 15/904,092, filed on Feb. 23, 2018, now Pat. No. 10,586,400.

(51) Int. Cl.
| | |
|---|---|
| *A61B 6/00* | (2006.01) |
| *G06T 7/11* | (2017.01) |
| *G06T 7/00* | (2017.01) |
| *G06T 15/08* | (2011.01) |
| *G06T 5/00* | (2006.01) |
| *G06T 5/50* | (2006.01) |

(52) U.S. Cl.
CPC ............ *A61B 6/583* (2013.01); *A61B 6/5217* (2013.01); *A61B 6/5258* (2013.01); *G06T 5/001* (2013.01); *G06T 5/50* (2013.01); *G06T 7/0014* (2013.01); *G06T 7/11* (2017.01); *G06T 15/08* (2013.01); *G06T 2207/10116* (2013.01)

(58) Field of Classification Search
None
See application file for complete search history.

(56) References Cited

U.S. PATENT DOCUMENTS

| | | | |
|---|---|---|---|
| 2015/0178925 A1* | 6/2015 | Jo | A61B 6/502 382/131 |
| 2017/0039706 A1* | 2/2017 | Mikhno | G06T 15/08 |
| 2017/0148158 A1* | 5/2017 | Najarian | A61B 5/7203 |
| 2020/0380675 A1* | 12/2020 | Golden | G06T 7/0012 |

* cited by examiner

*Primary Examiner* — James A Thompson

(57) ABSTRACT

A method and apparatus is disclosed, which improves the analysis of an object within a scanned bag. Specifically, the techniques disclosed herein overcome the problem of measurement errors due to imaging artifacts, which can occur during imaging examinations like CT scans. This process also discloses a method of using an improved accuracy of data units of an object lead to more accurate classification of the material that makes up the object.

20 Claims, 30 Drawing Sheets

Table 500

| | A | B | C | D | E | F | G |
|---|---|---|---|---|---|---|---|
| 1 | Raw Data (Hounsfeld Unit) | Multiplier at time point #1 | Displayed Value at time point #1 | Multiplier at time point #2 Applied to Displayed Value #1 | Displayed Value at time point #2 | Multiplier at time point #3 Applied to Displayed Value #2 | Displayed Value at time point #3 |
| 21 | 20 | 1.2 | 24 | 1.2 | 28.8 | 1.2 | 34.56 |
| 22 | 21 | 1.2 | 25.2 | 1.2 | 30.24 | 1.2 | 36.288 |
| 23 | 22 | 1.2 | 26.4 | 1.2 | 31.68 | 1.2 | 38.016 |
| 24 | 23 | 1.2 | 27.6 | 1.2 | 33.12 | 1.2 | 39.744 |
| 25 | 24 | 1.2 | 28.8 | 1.2 | 34.56 | 1.2 | 41.472 |
| 26 | 25 | 1.2 | 30 | 1.2 | 36 | 1.2 | 43.2 |
| 27 | 26 | 1.2 | 31.2 | 1.2 | 37.44 | 1.2 | 44.928 |
| 28 | 27 | 1.5 | 40.5 | 1.5 | 60.75 | 1.5 | 91.125 |
| 29 | 28 | 1.5 | 42 | 1.5 | 63 | 1.5 | 94.5 |
| 30 | 29 | 1.5 | 43.5 | 1.5 | 65.25 | 1.5 | 97.875 |
| 31 | 30 | 1.5 | 45 | 1.5 | 67.5 | 1.5 | 101.25 |
| 32 | 31 | 1.5 | 46.5 | 1.5 | 69.75 | 1.5 | 104.625 |
| 33 | 32 | 1.5 | 48 | 1.5 | 72 | 1.5 | 108 |
| 34 | 33 | 1.5 | 49.5 | 1.5 | 74.25 | 1.5 | 111.375 |
| 35 | 34 | 2 | 68 | 2 | 136 | 2 | 272 |
| 36 | 35 | 2 | 70 | 2 | 140 | 2 | 280 |
| 37 | 36 | 2 | 72 | 2 | 144 | 2 | 288 |
| 38 | 37 | 2 | 74 | 2 | 148 | 2 | 296 |
| 39 | 38 | 2 | 76 | 2 | 152 | 2 | 304 |
| 40 | 39 | 2 | 78 | 2 | 156 | 2 | 312 |
| 41 | 40 | 2 | 80 | 2 | 160 | 2 | 320 |

| Example examination viewed | Optimal settings during 2D slice-by-slice imaging approach |
|---|---|
| Liver on CT | e.g., Liver is shaded in gray shades and with particular bands (e.g., specified range is designed to catch hypervascular tumors, necrotic tumors, etc.) in color with option for voxel manipulation. All other tissues are turned to dark gray shades. |
| Breast on digital breast tomosynthesis | e.g., Breast glandular parenchyma in gray shades with particular bands (e.g., specified range is designed to catch microcalcifications) shown in red and enlarged voxels (option). |

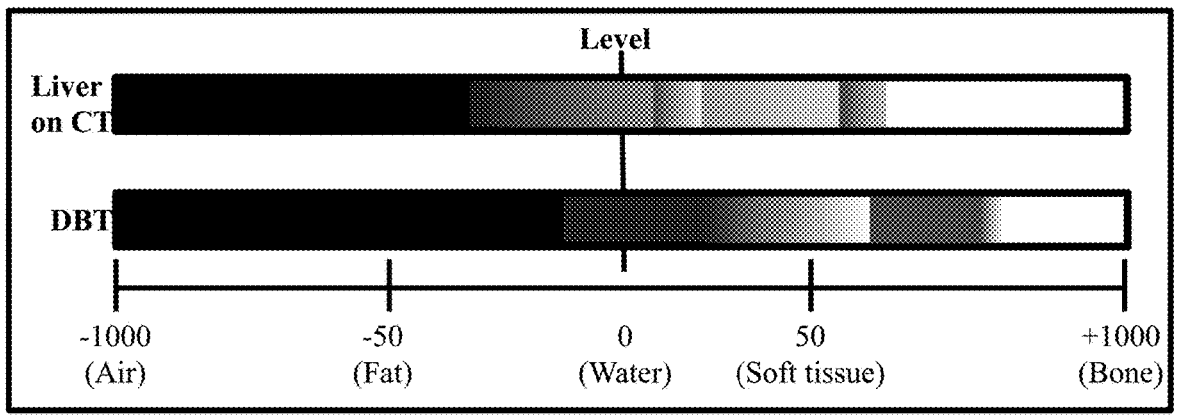

1102

1104

| Example item viewed | Optimal settings during 3D imaging (e.g., using XR headset) |
|---|---|
| Liver | e.g., Bands-wise prioritization of HU ranges is utilized within the liver and displayed in a dynamic fashion to make more subtle (but dangerous lesions) easier to detect. Implement prioritized volume rendering. All other tissues are made more translucent (e.g., sparse sampling) or are filtered. |
| Breast on DBT | e.g., Prioritized volume rendering is performed wherein the breast microcalcifications, which are of a higher priority and be displayed. All other tissues are made more translucent (e.g., sparse sampling) or are filtered. |

Figure 11

Illustration of generating multiple simultaneous window/level viewing settings for viewing of 3D datasets

Performing a first windowing and leveling setting
1300

Perform segmentation of organs
1301

Generating a list of data that might be normal vs abnormal.
1302

Applying a first visual representation adjustment logic to standard window/level setting to voxels that are thought to be normal.
1303

Applying second visual representation adjustment logic (false color) that are thought to be abnormal.
1304

Option to apply additional (third or more) visual representation adjustment logic to additional ranges
1305

Figure 13

- The following image is a subvolume of a CT scan of the breast, inside of a volume-subtending 3D cursor.
- The subvolume is comprised of approximately 100 x 100 x 100 or 1 million voxels.

1400

An embodiment of this patent is to be able to improve imaging by making some voxels (e.g., voxels with Hounsfield Unit range 70-75) to have a "special" visibility.

1407

Step #1
- Divide the voxels into ranges.
  - The first range will include all voxels with Hounsfield Units between 70 and 75. Assume that there are 3 voxels in this first band.
  - The second range will include all other voxels in the volume. Assuming the 100 x 100 x 100 matrix, that would equal 999,997 voxels in this second band.

Step #2
- Assign visual representation adjustment logic to the first band of 3 voxels (e.g., color all voxels in this band yellow)

Step #3
- Assign a different visual representation adjustment logic to the second band of 999,997 voxels (e.g., color voxels in this band varying shades of gray based on Hounsfield Units and conventional windowing and leveling settings.

1500

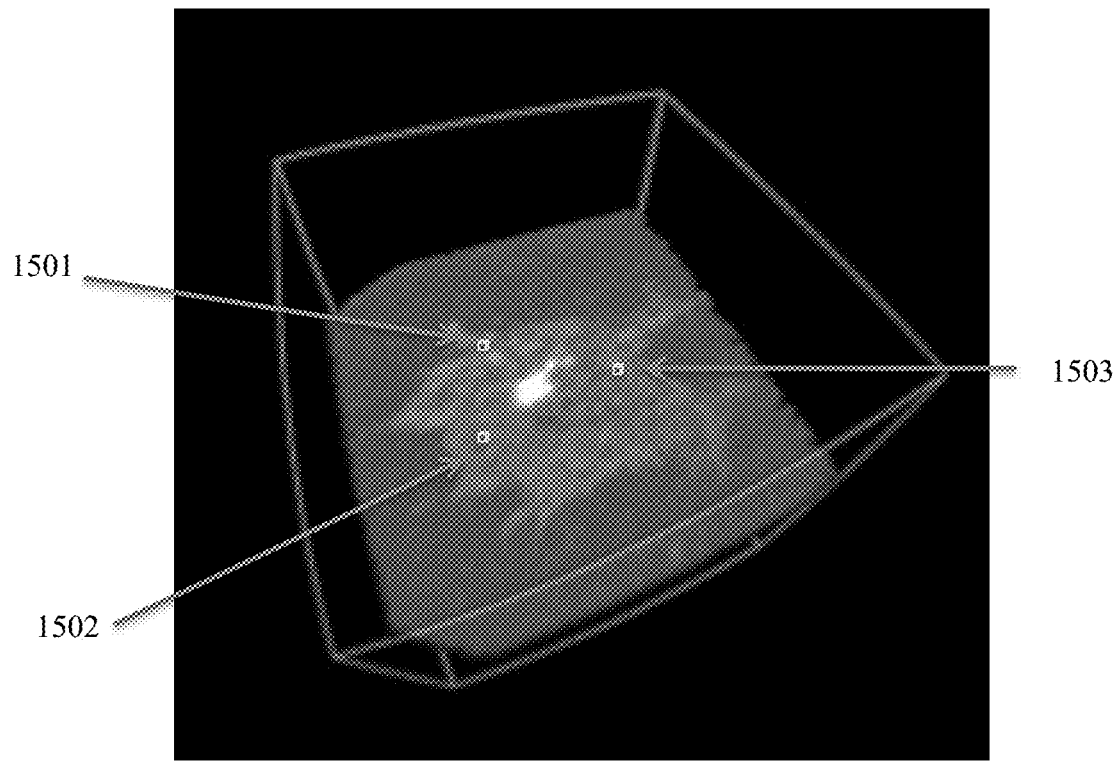

Figure 15

METHOD OF IMPROVING IMAGING QUALITY

Perform imaging examination
1600

Load an original imaging dataset of a patient wherein each pixel or voxel within the imaging dataset has an associated data unit
1601

Perform segmentation of the imaging dataset
1602

Select a first segmented structure for analysis
1603

Perform at least one measurement of the data unit(s) within the first segmented structure
1604

Determine the expected value(s) of the data unit(s) within the first segmented structure
1605

Determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality
1606

Input the at least one corrective factor to modify the data units of at least one of the group comprising the first segmented structure and the second segmented structure in the original imaging dataset to create a modified imaging dataset wherein the modified imaging dataset has improved image quality
1607

Figure 16

Fig. 19A
Fig. 19B
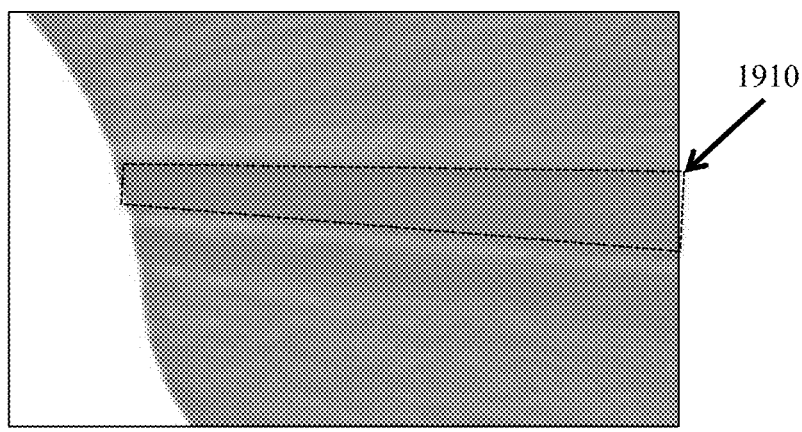
Fig. 19C
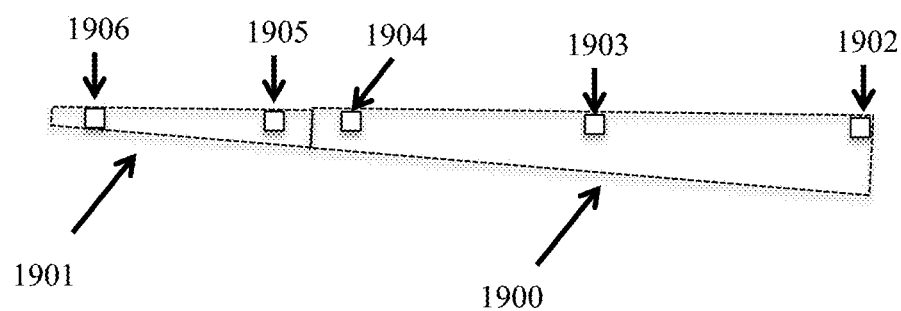
Figure 19

| 50 | 50 | -1000 | -1000 | -1000 |
|----|----|-------|-------|-------|
| 50 | 50 | -1000 | -1000 | -1000 |
| 40 | 40 | -990  | -990  | -990  |
| 50 | 50 | -1000 | -1000 | -1000 |
| 50 | 50 | -1000 | -1000 | -1000 |

2500

| 50 | 50 | -1000 | -1000 | -1000 |
|----|----|-------|-------|-------|
| 50 | 50 | -1000 | -1000 | -1000 |
| 50 | 50 | -1000 | -1000 | -1000 |
| 50 | 50 | -1000 | -1000 | -1000 |
| 50 | 50 | -1000 | -1000 | -1000 |

2501

GENERATING A CUSTOMIZED VOLUME TO OPTIMIZE ACCURACY OF MEASUREMENT 2801A
2802A
2800A 2801B
2802B
2800B

GENERATING MULTIPLE CUSTOMIZED VOLUMES AND USING
WEIGHTING FACTORS TO OPTIMIZE ACCURACY OF MEASUREMENT

GENERATING A MODIFIED IMAGE USING ARTIFICIAL INTELLIGENCE

METHOD AND APPARATUS FOR IMPROVING CLASSIFICATION OF AN OBJECT WITHIN A SCANNED VOLUME

CROSS REFERENCE TO RELATED APPLICATIONS

The present application is a continuation-in-part of U.S. patent application Ser. No. 16/752,691 filed on Jan. 26, 2020, which is a continuation-in-part of U.S. Ser. No. 15/904,092 filed on Feb. 23, 2018. All of these related applications are incorporated by reference.

TECHNICAL FIELD

Aspects of the present disclosure are generally related to processing three-dimensional image data, more specifically to improving image quality.

BACKGROUND

Known techniques for 3D viewing of medical images are described in U.S. Pat. No. 9,349,183, Method and Apparatus for Three Dimensional Viewing of Images, issued to Douglas, U.S. Pat. No. 8,384,771, Method and Apparatus for Three Dimensional Viewing of Images, issued to Douglas, Douglas, D. B., Petricoin, E. F., Liotta L., Wilson, E. D3D augmented reality imaging system: proof of concept in mammography. Med Devices (Auckl), 2016; 9:277-83, Douglas, D. B., Boone, J. M., Petricoin, E., Liotta, L., Wilson, E. Augmented Reality Imaging System: 3D Viewing of a Breast Cancer. J Nat Sci. 2016; 2(9), and Douglas, D. B., Wilke, C. A., Gibson, J. D., Boone, J. M., Wintermark, M. Augmented Reality: Advances in Diagnostic Imaging. Multimodal Technologies and Interaction, 2017; 1(4):29.

SUMMARY

All examples, aspects and features mentioned in this document can be combined in any technically possible way.

In accordance with an aspect an apparatus comprises: a controller; and an image processing system that generates a three-dimensional image comprising voxels corresponding to image data of a scanned volume, the image data comprising radiodensity values, the image processing system comprising visual representation adjustment logic that adjusts selected ones of the voxels based on selected ones of the radiodensity values, wherein the visual representation adjustment logic is configured in response to commands provided via the controller. Some implementations further comprise segmentation logic that performs segmentation, wherein the segmentation logic is configured in response to commands provided via the controller. Some implementations further comprise filtering logic that performs filtering, wherein the filtering logic is configured in response to commands provided via the controller. In some implementations the visual representation adjustment logic changes a grayscale value of the selected voxels. In some implementations the visual representation adjustment logic changes a color value of the selected voxels. In some implementations the visual representation adjustment logic increases dynamic range of the selected voxels. In some implementations the visual representation adjustment logic changes size of the selected voxels. In some implementations the visual representation adjustment logic changes shape of the selected voxels. In some implementations the visual representation adjustment logic changes orientation of the selected voxels. In some implementations the visual representation adjustment logic demarks the selected voxels with color. In some implementations the visual representation adjustment logic is temporally adjusted to present versions of an image corresponding to different configuration settings. In some implementations the filtering logic removes some of the selected voxels from the three-dimensional image. In some implementations the filtering logic is temporally adjusted to present versions of an image corresponding to different filter configuration settings. In some implementations the segmentation logic classifies a voxel under consideration based on the tissue type of nearest neighbor voxels in a matrix. In some implementations the segmentation logic fills a gap in a structure. In some implementations the image processing system generates multiple images from the image data using different configuration settings, and combines the multiple images to generate the three-dimensional image as a composite image.

In accordance with an aspect, a method comprises: in an image processing system, generating a three-dimensional image comprising voxels corresponding to image data of a scanned volume, the image data comprising radiodensity values, wherein generating the three-dimensional image comprises: configuring visual representation adjustment logic with configuration settings in response to commands provided via a controller; and adjusting selected ones of the voxels based on selected ones of the radiodensity values in accordance with the configuration settings. Some implementations further comprise configuring segmentation logic in response to commands provided via the controller, and performing segmentation. Some implementations further comprise configuring filtering logic in response to commands provided via the controller, and performing filtering. In some implementations adjusting selected ones of the voxels comprises changing a grayscale value of the selected voxels. In some implementations adjusting selected ones of the voxels comprises changing a color value of the selected voxels. In some implementations adjusting selected ones of the voxels comprises increasing dynamic range of the selected voxels. In some implementations adjusting selected ones of the voxels comprises changing size of the selected voxels. In some implementations adjusting selected ones of the voxels comprises changing shape of the selected voxels. In some implementations adjusting selected ones of the voxels comprises changing orientation of the selected voxels. In some implementations adjusting selected ones of the voxels comprises demarking the selected voxels with color. In some implementations adjusting selected ones of the voxels comprises temporally adjusting configuration values to present versions of an image corresponding to different configuration settings. Some implementations comprise the filtering logic removing some of the selected voxels from the three-dimensional image. Some implementations comprise temporally adjusting the filtering logic to present versions of an image corresponding to different filter configuration settings. Some implementations comprise the segmentation logic classifying a voxel under consideration based on the tissue type of nearest neighbor voxels in a matrix. Some implementations comprise the segmentation logic filling a gap in a structure. Some implementations comprise the image processing system generating multiple images from the image data using different configuration settings, and combining the multiple images to generate the three-dimensional image as a composite image.

The purpose of this continuation-in-part patent is to teach a method to improve image quality. This is useful because improved image quality can yield more accurate diagnosis of disease and lead to better treatment strategies. The methods disclosed include utilization of data unit assurance markers within the field of view of an imaging examination to improve image quality. Examples of data unit assurance markers are discussed throughout this patent, but serve as a trusted landmark of a radiodensity data unit (e.g., Hounsfield Unit in CT, Intensity unit in MRI, etc.). The preferred embodiment of this invention is the incorporation of at least one, but preferably multiple data unit assurance markers into the field of view of an image, such that through processed disclosed below, the data units of voxels or pixels in the data set can be modified. With modifications guided by the data unit assurance markers, the trustworthiness of the data is improved and diagnosis is also improved. The preferred embodiment is to utilize this process in medical imaging; however, this process can be used in any type of image processing techniques, whether it be 2D or 3D datasets.

A method and apparatus is disclosed, which significantly improves image quality. Specifically, the method disclosed utilizes structures within an image with a known or calculated value, such as a phantom or presumed homogeneous structure, such as an air mass outside of the patient. The method then performs segmentation of the imaging dataset and subsequent measurement of the structure with a known value. The difference between the known value and the measured value is used as a correction factor, which is then applied to the remainder of the dataset where values are not known. This can improve image quality by helping to generate extremely similar gray scale maps over multiple examinations and eliminate artifacts.

The preferred embodiment includes multiple steps. The first step is loading an original imaging dataset of a patient wherein each pixel or voxel within the imaging dataset has an associated data unit. Examples of this dataset include, but are not limited to, a chest radiograph comprised of pixels and a head computed tomography (CT) comprised of voxels. Next, is performing segmentation of the imaging dataset. The preferred segmentation strategies is by data unit. Other anatomic atlas based segmentation strategies can also be implemented, such as the Talairach atlas. Note that the preferred embodiment is for all voxels in the dataset to be segmented including voxels outside of the patient's anatomy. Next, select a first segmented structure. For example, the air outside of the patient is selected. Next, perform at least one measurement of the data unit(s) within the first segmented structure. For example, measurements of Hounsfield Units of the air is performed. Next, determine the expected value(s) of the data unit(s) within the first segmented structure. The preferred embodiment is to use look up tables. For example, a look up table shows that air at standard temperature and pressure is −1000 Hounsfield Units (e.g., see https://radiopaedia.org/articles/hounsfield-unit?lang=us). An alterative embodiment is to determine which structures are homogeneous. For example, air outside the patient should be substantially (approximately) homogeneous. Thus, the mean Hounsfield unit can be calculated and this calculated number used instead of the −1000 from the look up table. Next, determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality.

The variation of the Hounsfield Units in the body can be related to normal tissue planes, not streak artifact. Therefore, it is difficult to perform reliable streak artifact correction by examining the tissues inside of the body alone. Thus, the preferred embodiment for streak artifact correction is to use the air. A map of the air should have homogenous Hounsfield units. If patterns (e.g., linear, triangular or trapezoid shaped) of hyperattenuation or hypoattenuation are present, then characterization of streak artifact is possible. For example, assume there is a linear-type pattern of streak artifact emanating through the brain, skull and scalp and then continuing through the air. The portion of air can be measured and analyzed. For example, the air is assumed to be −990 over a linear group, rather than the −1000. A corrective factor can be established for the air, anatomical structures (e.g., brain, skull, scalp) or combination thereof. Next, input the at least one corrective factor to modify the data units of at least one of the group comprising the first segmented structure and the second segmented structure in the original imaging dataset to create a modified imaging dataset wherein the modified imaging dataset has improved image quality. Modifications to Hounsfield Units in the dataset is performed, such that a new dataset with improved image quality is established.

In some embodiments, the method comprises wherein the selected first segmented structure is located external to the patient. Examples, include, but are not limited to, the following: air; water; and, a phantom containing multiple substances to mimic human body tissues (e.g., fat, blood, organs, bone, etc.), surgical objects, etc.

Some embodiments comprise a variety of techniques for selection of a segmented region for analysis of aberrations (e.g., the streak artifact coursing through the air as described above). The preferred embodiment is analyzing a structure wherein the data value is known, such as a phantom filled with known substances. Alternative embodiments comprise analyzing a structure whose property is known to be homogenous (e.g., air can be assumed to be homogeneous). Another alternative embodiment is analyzing an structure whose material property is known to be inhomogeneous, but predictable. This could be foam padding or fluid-type materials that layer in a predictable fashion.

Some embodiments comprise wherein the selected first segmented structure outside of the patient is at least one of the group comprising air outside of the patient, a phantom outside of the patient, a surgical object whose physical properties and imaging appearances are known and other objects which are commonly present in the scanner whose physical properties can be determined.

Some embodiments comprise wherein the selected first segmented structure is located internal to the patient. Examples include, but are not limited to the following: pacemaker, orthopedic hardware, surgical tubing, internal placement of phantoms, anatomic structures with predictable physical properties (e.g., urine) or other objects inside the patient.

Some embodiments comprise wherein the first segmented structure is one of the group comprising surgical devices, fluid compartments, and anatomic structures that are substantially fixed over time, or change over time in a predictable manner. If a substance changes over time in a predictable fashion, then look up tables may be established. Some embodiments comprise wherein a database of imaging appearance of surgical hardware whose material properties and data value is known is utilized for the corrective factor. Again, a look up table may be established.

Some embodiments comprise wherein the second segmented structure is inside the body. This second segmented structure can include an anatomic feature, such as the brain. Some embodiments comprise wherein the application of the corrective factor corrects for imaging artifacts. For example, a streak artifact causing an artificially low density coursing across a gyri of the brain can be corrected for by adding a certain number of Hounsfield Units back to the affected gyri to restore it to the true level, as if it were never affected by the streak artifact.

Some embodiments comprise wherein an array of corrective factors are determined and applied to a plurality of data units in the imaging dataset. For example, alterations in the air in the front of the head and at the side of the head can be analyzed together to determine the corrective factor that should be implemented.

Some embodiments comprise wherein a user can review the modified imaging dataset for qualitative and quantitative analysis. For example, the user can view the corrected dataset, which is unhindered by the streak artifact. The user can measure a Hounsfield Unit in a CT scan of the adrenal glands and then accurately be able to characterize a lesion. For example, radiomics analysis (e.g., histograms) can be performed on the corrected dataset.

Some embodiments comprise placing a patient in the field of view of a scanning system along with at least one phantom in the field of view of the scanning system. The next step is performing a scan containing both the patient and the at least one phantom in the scanner. This serves to provide reliable landmark(s) present during the examination to use for correction. Some embodiments comprise wherein a single or multiple phantoms are present in each imaging slice. The preferred embodiment is for the use of multiple phantoms to be placed in each imaging slice.

Some embodiments comprise wherein a user can perform windowing and leveling such that a grayscale appearance of a phantom on a first imaging examination substantially matches a grayscale to a phantom on a second imaging examination. Some embodiments comprise wherein a grayscale appearance of a phantom is used to guide the exposure of a radiograph to prevent over-exposure and to prevent under-exposure. The x-ray detector could use the information related to the number of photons that have passed through the phantom and onto the x-ray detector to determine exposure in real time, so as to prevent under-exposure and over-exposure. Additionally, for example, a chest x-ray can be performed in Florida in July 2020 with a x-ray detector and a phantom in the field of view. Then, a chest x-ray can be performed in Georgia in July 2021 with a completely different x-ray detector and phantom in the field of view. The radiologist can then match the gray scale appearance of the phantom(s) on the July 2020 imaging examination with the gray scale appearance of the phantom(s) on the July 2021 imaging examination, such that the gray scale images are substantially similar by windowing and leveling to such that each of the elements in the phantom (e.g., fat, calcium, air, etc.) appear the same brightness level (e.g., in $cd/m^2$) on the July 2020 imaging examination and the July 2021 imaging examination. Additionally, this process can be used in accordance with 62/959,918, Multi-dimensional Imaging Window, such as is described throughout the entire patent, but especially in FIGS. 1-2.

Some embodiments comprise wherein multiple phantoms are placed inside the body. For example, a patient can be instructed to swallow multiple slow dissolving capsules with characteristic radiographic signatures (e.g., water, oil, etc.). These can be used as internal phantoms in conjunction with other processed discussed in this patent.

Some embodiments comprise wherein a grayscale appearance of a phantom is used to determine whether the exposure of a radiograph is adequate. The preferred embodiment to perform this is via photon counting metrics at the site of the phantom.

Some embodiments comprise wherein the at least one phantom is placed inside one of the group of a wrap (e.g., blanket) surrounding the patient, the gurney, a coil, a table, a backboard, or other apparatuses commonly present inside of a scanner.

Some embodiments comprise an apparatus comprising: an x-ray detector; and, a phantom connected to the x-ray detector. This apparatus is useful because it can to enhance the quality of radiographs and to make the dose the lowest possible to achieve diagnostic quality image.

Some embodiments comprise an apparatus comprising: an IO device; and an image processor in communication with the IO device, the image processors comprising a program stored on a computer-readable non-transitory media, the program comprising instructions that perform: a step for loading an original imaging dataset of a patient wherein each pixel or voxel within the imaging dataset has an associated data unit; a step for performing segmentation of the imaging dataset; a step for selecting a first segmented structure for analysis; a step for performing at least one measurement of the data unit(s) within the first segmented structure; a step for determining the expected value(s) of the data unit(s) within the first segmented structure; a step for determining at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality; and a step for imputing the at least one corrective factor to modify the data units of at least one of the group comprising the first segmented structure and the second segmented structure in the original imaging dataset to create a modified imaging dataset wherein the modified imaging dataset has improved image quality.

The purpose of this invention is also to improve efficiency and accuracy of understanding images. The preferred embodiment of this invention is to a method that a radiologist can use to improve the ability to compare a first imaging examination with a second imaging examination. For example, it the multi-dimensional imaging window process, as disclosed in U.S. Provisional Patent No. 62/959,918, multi-dimensional imaging window, that the same window and leveling settings on a CT scan can result in slight differences in the appearance of anatomic structures of the gray scale of an image. The method and apparatus disclosed in this patent overcome the problem of variability of data units (e.g., Hounsfield Units) of structures in between examinations (e.g., performed on scanner #1 vs scanner #2).

In some embodiments, consistency can be performed by placing one or more phantoms in the scanner in with the patient. The phantoms could be designed to have a variety of different material properties. For example, the phantoms could be designed with multiple compartments including oil, water, air, calcium, and soft tissue. The preferred embodiment is for the phantoms to be located in the table of the scanners (e.g., CT and MRI). Alternatively, a blanket with hundreds or even thousands of small phantoms can cover the patient during the scanner acquisition. Additionally, the phantoms can be arranged in a variety of arrangements, which include, but are not limited to, the following: a single, non-circumferential arrangement; a single circumferential arrangement; multiple layers of non-circumferential arrangement; multiple circumferential layers of arrangement; and, other arrangement patterns.

In some embodiments, the multi-dimensional imaging window, as disclosed in as disclosed in U.S. Provisional Patent No. 62/959,918, multi-dimensional imaging window can be performed, discussed throughout the whole patent, but especially in FIGS. 1-2. A structure of the same material property that is spans across a first imaging examination and a second imaging examination should have the same data units (e.g., Hounsfield units). In some embodiments, a first image is transformed to look like a second image. Several spots within the imaging dataset can be selected as "consistency" spots, to serve as pseudo-phantoms.

In some embodiments, these techniques can correct for intra-machine differences, such as a change in scanner performance over time. For example, these techniques can correct for intra-machine differences over time. In some embodiments, these techniques can correct for inter-machine differences, such as a GE CT scanner and a Siemens CT scanner.

In some embodiments, these techniques can correct for areas of decreased signal (e.g., related to a coil in an MM scan).

A scan could be a computed tomography (CT) examination, a magnetic resonance imaging (MM) examination, a magnetic resonance angiography (MRA) examination, a computed tomography angiography (CTA) examination, etc. or similar type scanning techniques.

A phantom is a device which contains compartments with known material properties, which can be used in conjunction with a scanner.

Some embodiments comprise performing an imaging examination of a volume to generate a 3D dataset, performing segmentation of an object within the 3D dataset and performing an analysis to determine whether said object contains an imaging artifact. If said imaging artifact is identified, designing a customized volume to exclude said imaging artifact. Next, perform a measurement of data units within said customized volume. Then, compare said measurement of data units with a material classification database wherein said material classification database contains data units associated with a list of known type of materials. For example, assume that the imaging examination is a CT scan. A list of known type of materials and their known Hounsfield Units can be used (e.g., water has Hounsfield Units of 0, Copper has Hounsfield Units of 14,000, Steel has Hounsfield Units of 20,000, Limestone has Hounsfield Units of 2,800, glass has Hounsfield Units of 500, and so on.) Finally, classify a material of said object based on at least said comparing said measurement data units with said material classification database. Note that these techniques can be used in conjunction with those taught in U.S. patent application Ser. No. 17/164,772, A METHOD AND APPARATUS FOR PRESENTING A PRE-FILTERED IMAGE TO A USER FOR ANALYSIS, filed on Feb. 1, 2021, which is incorporated by reference in its entirety. Some embodiments further comprise wherein said imaging examination is a CT scan or an MRI scan. Some embodiments comprise wherein said imaging examination is a LIDAR scan. Some embodiments further comprise wherein said customized volume is an sphere, cylinder, cube or irregular shape. Some embodiments further comprise wherein data units outside of the segmented boundary of the object are analyzed to characterize said imaging artifact. Some embodiments comprise wherein said performing an analysis to determine whether said object contains said imaging artifact comprises an artificial intelligence algorithm. Some embodiments comprise wherein data unit assurance markers assist in performing an analysis to determine whether said object contains an imaging artifact.

Some embodiments comprise a method of performing an imaging examination of a volume to generate a 3D dataset, performing segmentation of an object within said 3D dataset, and performing an analysis to determine whether said object contains an imaging artifact. If said imaging artifact is identified, a correction of said imaging artifact can be performed. This correction would alter the data units. Some embodiments comprise performing a measurement of data units within said object and comparing said measurement of data units with a material classification database wherein said material classification database contains data units associated with a list of known type of materials. Next, classify a material of said object based on at least said comparing said measurement data units with said material classification database. Some embodiments comprise wherein said imaging artifact is segmented to precisely delineate the boundary of the artifact. Some embodiments comprise wherein data units outside of said object are analyzed to characterize said imaging artifact. Some embodiments comprise wherein said correction of said imaging artifact is performed using an artificial intelligence algorithm to generate a modified dataset. Some embodiments comprise wherein the modified dataset is displayed to said user. Some embodiments comprise wherein data unit assurance markers assist in performing an analysis to determine whether said object contains an imaging artifact. Some embodiments comprise wherein said data unit assurance markers comprise at least one of the group consisting of: a phantom; a homogeneous structure whose data value is unknown; and a heterogeneous structure whose data value is unknown, but predictable.

Some embodiments comprise performing an imaging examination of a volume to generate a 3D dataset, performing segmentation of an object within said 3D dataset, performing an analysis of said object wherein a first portion of said object contains an imaging artifact and a second portion of said object does not contain an imaging artifact, performing a measurement of data units within said second portion, comparing said measurement of data units with a material classification database wherein said material classification database contains data units associated with a list of known type of materials, and classifying a material of said object based on at least said comparing said measurement data units with said material classification database. Some embodiments comprise generating a visible boundary of said second portion. Some embodiments comprise generating a visible boundary of said first portion. Some embodiments comprise performing a second measurement of data units within said first portion. Some embodiments comprise using a first weighting factor for the first portion and a second weighting factor for the second portion to determine a composite measurement of data units. Some embodiments comprise performing an analysis of changes in data units in the gravity-dependent layers of said object.

BRIEF DESCRIPTION OF THE FIGURES

The patent or application file contains at least one drawing executed in color. Copies of this patent or patent application publication with color drawing(s) will be provided by the Office upon request and payment of the necessary fee.

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that the particular sequence of steps described is illustrative only and can be varied without departing from the spirit of the invention. Thus, when possible, the steps can be performed in any convenient or desirable order.

FIG. 5 illustrates mathematical adjustments of voxels to enhance discrimination between voxels based on grayscale values.

FIG. 11 illustrates optimal viewing settings for 2D imaging and for 3D imaging.

FIG. 13 illustrates generating multiple simultaneous window/level settings for viewing of 3D datasets.

FIG. 15 illustrates with overcoming challenges in visualizing certain ranges when using viewing multiple windowing.

FIG. 16 illustrates a method of improving image quality.

FIG. 19A illustrates a CT image of the head with window and level settings optimized for visualization of air.

FIG. 19B illustrates a zoomed in CT image of the head with window and level settings optimized for visualization of air.

FIG. 19C illustrates a plot of voxels within the region of air, which can be used to determine the correction factor applied to voxels within the head.

DETAILED DESCRIPTION

Figure 1:
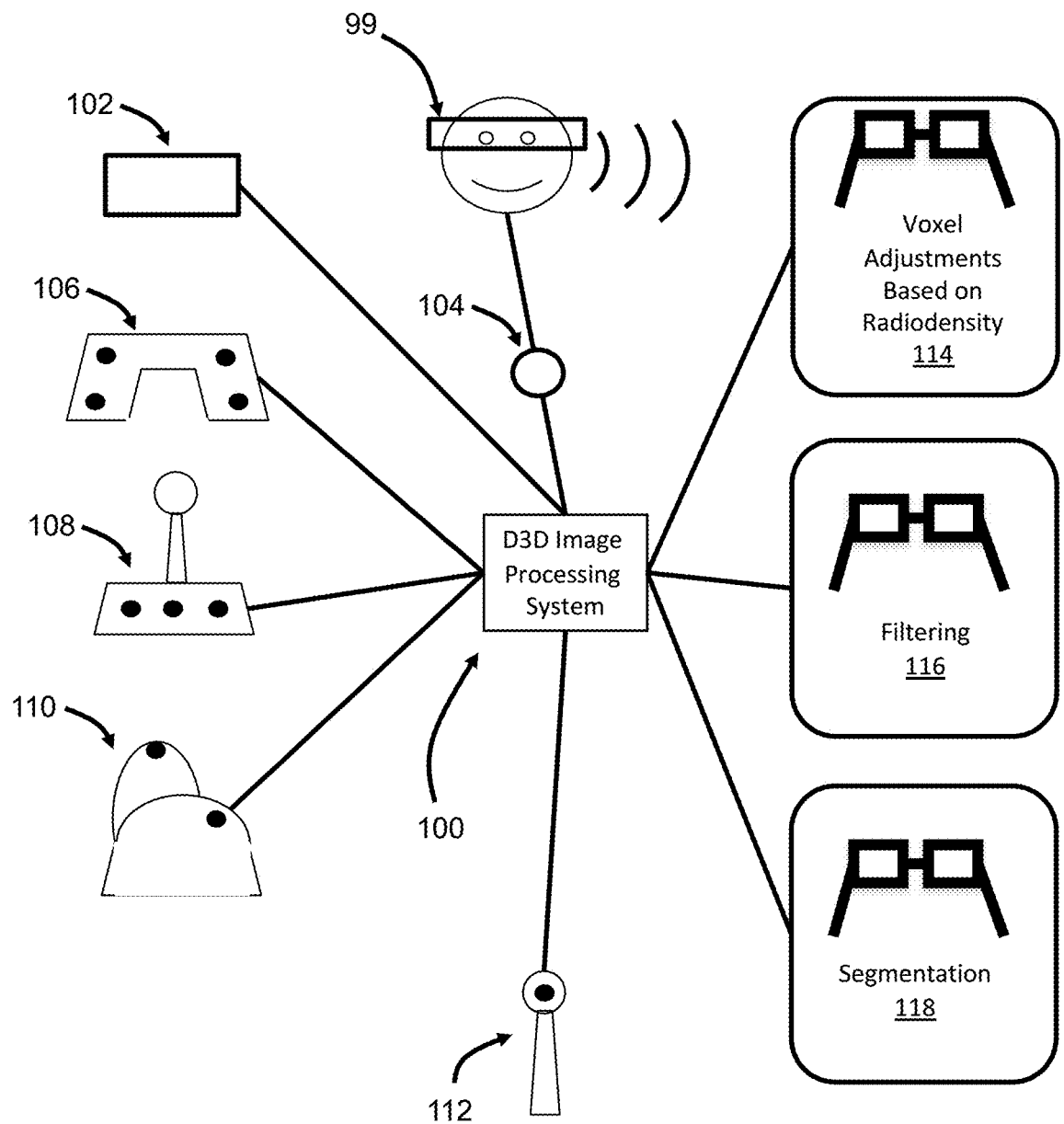
FIG. 1 illustrates a D3D image processing system.

Some aspects, features, and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

In a D3D imaging system, a radiologist uses a controller to manipulate 3D (three-dimensional) images that may be viewed via special glasses or a VR (virtual reality) headset. The 3D images may be generated from radiological scan data, for example and without limitation from X-ray radiography, CT (computed tomography), PET (positron emission tomography), or MM (magnetic resonance imaging). There will normally be a linear relationship between density or radiodensity values from the scan data and the grayscale values assigned to corresponding voxels of the 3D images. Advantages of existing examples may include improved depth perception and an improved human machine interface. Still, there are several challenges faced with this approach. First, an area of interest (e.g. tumor) may be in close proximity to structures that are similar in composition/density. Isolating the area of interest for better examination may be difficult. Second, many soft tissues in the body are mobile and deformable, so it can be difficult to achieve the best orientation to properly compare the tumor at multiple time points. Efficiently aligning the orientation to do so may be difficult. Third, certain portions of a tumor can respond to treatment and decrease in size while other portions of a tumor demonstrate increases in size. The pattern of tumor shrinkage has important prognostic implications. Furthermore, composition and complex morphologic features including speculations (spikes extending from the surface), irregular margins and enhancement also have important implications. Consequently, there is a need for a system that facilitates recognition of the subtle, yet important changes in size, shape and margins. Fourth, a patient with metastatic cancer has several areas of interest in different areas of the body. It is difficult and time consuming to find each of the areas of interest at every time point to determine interval change. Consequently, there is a need for a system that enables the observer to do this efficiently.

FIG. 1 illustrates an improved D3D image processing system 100 and various types of controllers and a VR headset 99 that interface with the D3D image processing system. A wide variety of controllers may be utilized, possibly including but not limited to one or more of a keyboard 102, microphone 104 (for voice control), hand held game-type controller 106, joy stick 108, high-end mouse 110, and wand 112. The controllers are used to enter commands that control an application that processes 3D image data and displays that 3D image data. As will be explained in greater detail below, the controllers are used to select, configure and implement image processing techniques including: voxel adjustments based on radiodensity 114; filtering 116; and segmentation 118.

Figure 2:
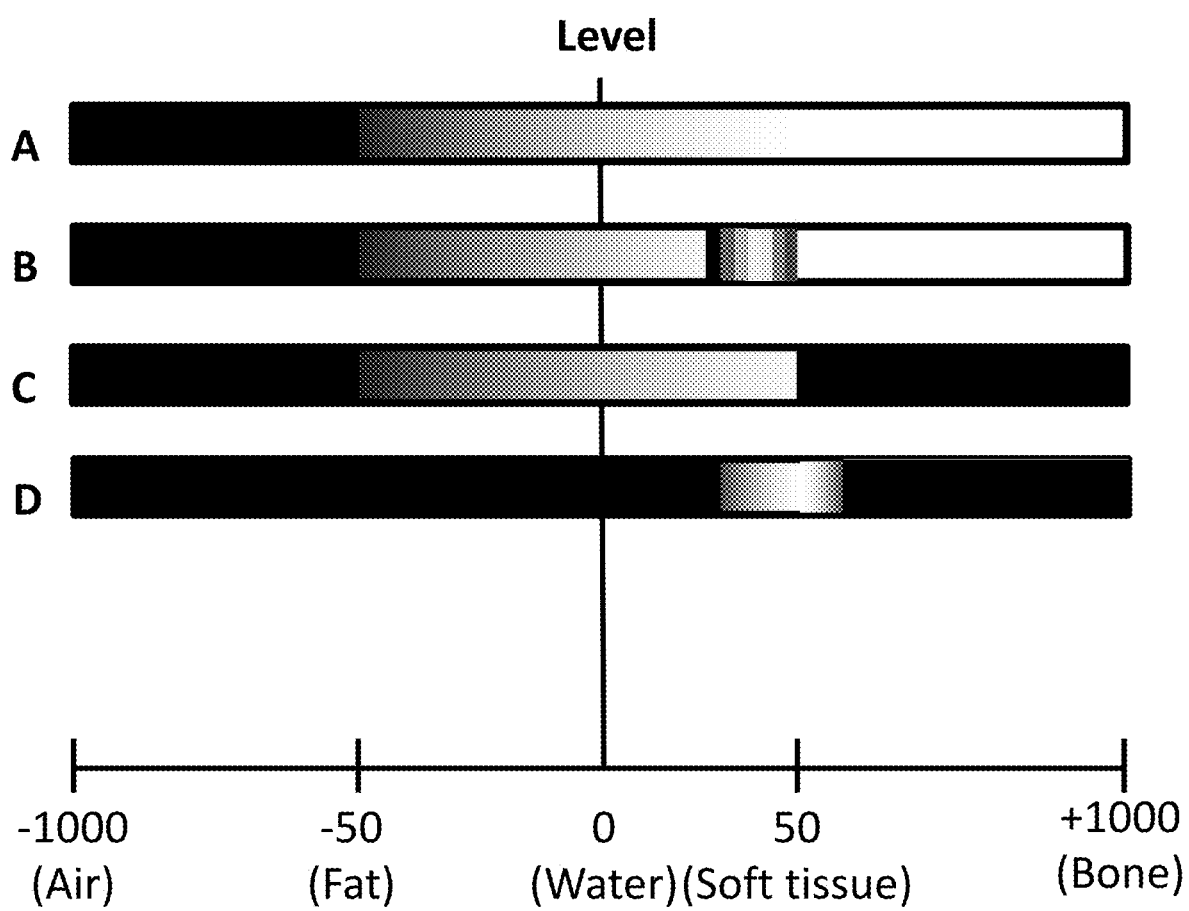
FIG. 2 illustrates aspects of voxel adjustments based on radiodensity in greater detail.

Referring to FIG. 2, an aspect of voxel adjustments based on radiodensity is grayscale and color adjustments. Raw 3D image data may include radiodensity values for locations in a scanned volume. Initially, grayscale and/or color values that are linearly related to radiodensity values may be assigned to voxels of an image corresponding to the 3D image data. Grayscale and/or color values corresponding to selected radiodensity values may then be adjusted for image enhancement. In the illustrated example, relative radiodensity values are used, namely HU (Houndsfeld Units). Initially assigned grayscale values may be linearly related to the HU values. Controller-entered commands enable the radiologist to independently adjust the relationship between HU values and grayscale and/or color values, e.g. from linear to non-linear. This may advantageously enhance presentation of tissue types of interest. In figure line A of the illustrated example, air within the body is initially shown in grayscale as black, whereas bone is shown as white. In line B, false color has been added to a region corresponding to an HU range that represents soft tissue. Selection, configuration, and application occur in response to controller-entered commands. In line C, grayscale values corresponding to HU values above a specified level have been changed to black (or not included in the voxel set displayed). In line D, grayscales values both above and below an HU range have been changed to black (or not included in the voxel set displayed). Tissues and other features may be distinguished based on radiodensity. Consequently, features and tissues may be selected, enhanced, and excluded based on radiodensity.

Although radiodensity is described herein as a basis for selection, it should be understood that a variety of related values, analogs, or proxies could be used instead of, or to represent, radiodensity. For example, and without limitation, tissue density could be used for selection. Further, a grayscale value, or range of values, could be directly selected and adjusted. The term radiodensity as used herein is intended to encompass all related values, analogs, and proxies.

Another aspect of voxel adjustments based on radiodensity is increasing the dynamic range of the displayed voxels. A process to achieve this may involve the following steps: selecting a volume of interest; removing all external tissue; setting a lower bound level of interest and a top bound; removing all tissue external to these bounds; extending the bounds by a factor of a selected factor (e.g., 2 or 10); and interpolating voxel grayscale values between the two bounds. This will have the effect of increasing dynamic range. Humans can only distinguish 7-8 bits of grayscale. This expansion of the upper/lower bounds would distinguish 10 bits or more, thus enabling the possibility of earlier and/or improved detection rate of tumors.

Figure 3A:
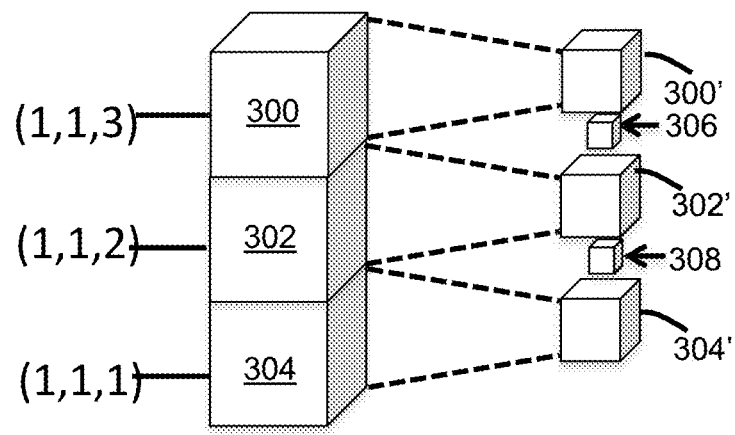
FIGS. 3A, 3B, and 3C illustrate adjustment of voxel size, shape, and orientation, respectively.

As shown in FIG. 3A, another aspect of voxel adjustments based on radiodensity is changing voxel size via controller-entered commands. For example, voxels having a selected radiodensity, or within a selected range, are adjusted in size by a selected magnitude. This technique may be used to cause a corresponding tissue type to be presented as semi-transparent. In the illustrated example, voxels 300, 302, 304 are reduced in size, yielding corresponding voxels 300', 302', 304', thereby permitting visualization of voxels 306, 308 that are more distant from the viewing point, i.e. deeper in the volume. Consequently, features can be seen that would otherwise have been occluded by the size-adjusted voxels in the near field of view.

Figure 3B:
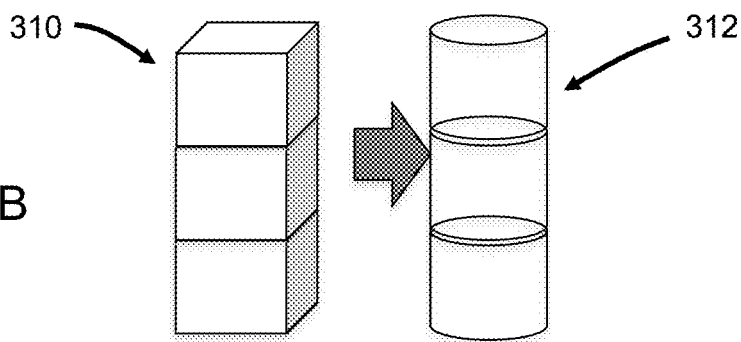

Referring to FIG. 3B, another aspect of voxel adjustments based on radiodensity is changing the shape of voxels via controller-entered commands based on radiodensity or some other basis. In the illustrated example, standard cubic voxels 310 having a selected radiodensity, or within a selected range, are adjusted to generate corresponding cylindrical voxels 312. Voxel shape may be selected to allow a smoother presentation of a feature being observed. For example, blood vessels could be better represented by cylindrical voxels as opposed to a column of cubes.

Figure 3C:
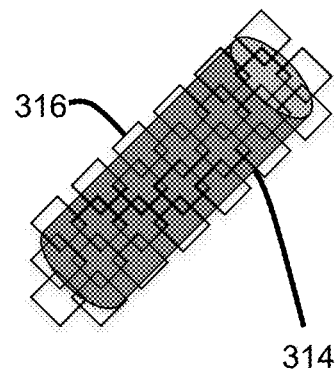

Referring to FIG. 3C, another aspect of voxel adjustments based on radiodensity is changing voxel orientation via controller-entered commands. In the illustrated example voxel orientation is changed from alignment with standard X, Y, Z axes as shown in FIG. 3A, to a slanted coordinate system that more closely aligns with the with the patient's anatomy. For example, voxel orientation may be changed to more closely represent the curvature of body contents to include tissues or surgical devices. In the illustrated example the voxel orientation is adjusted relative to a blood vessel 314 by adjusting axes of the sides or edges 316 of the voxels. Voxels associated with the blood vessel or other tissue types may be selected based on radiodensity or some other basis.

Figure 4A:
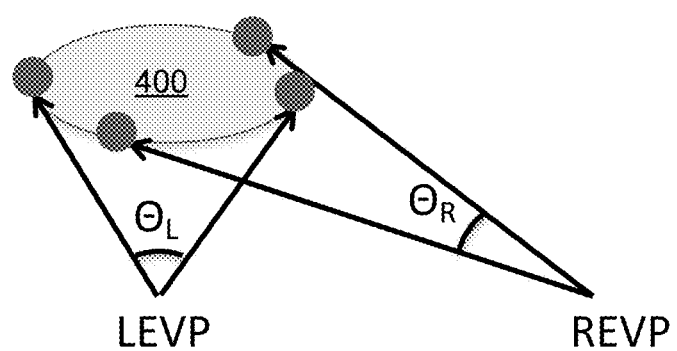
FIGS. 4A and 4B illustrate feature demarcation.
Figure 4B:
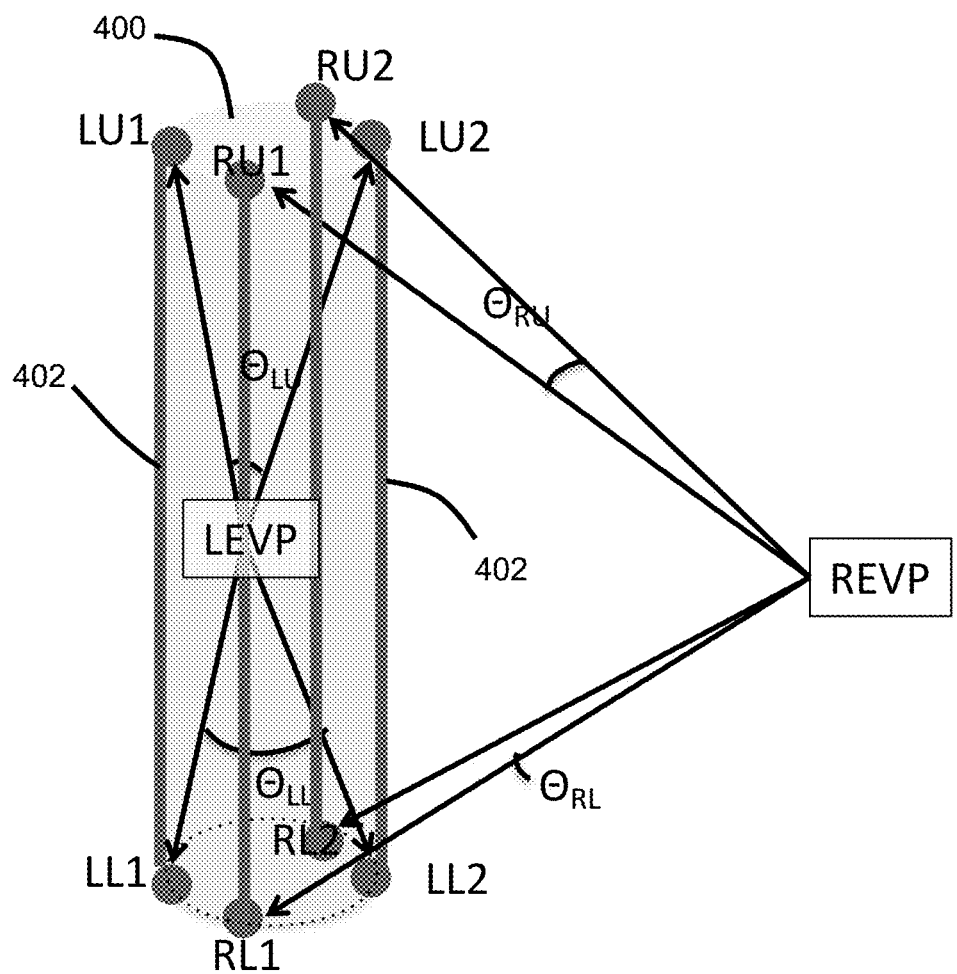

Referring to FIGS. 4A and 4B, another aspect of voxel adjustments based on radiodensity is feature demarcation. In the illustrated example, voxels associated with a vein 400 are demarked with blue lines 402 to enhance visualization. Although a vein is shown as an example, a wide variety of features and tissues may be demarked. Further, a wide variety of colors could be used, for example and without limitation, red lines could be generated to demark arteries. This is one of several potential uses of false color to facilitate medical personnel understanding of complex anatomy. Selection of whether to apply false color and to which types of tissue would be via a controller at the discretion of the medical personnel viewing the images. Voxels associated with the vein may be selected based on radiodensity or some other basis.

Some implementations may include showing the volume subtended by a cursor during review. This would permit, for example, an opportunity for the radiologist to ensure a thorough examination had been conducted and see if any regions had been missed. In some implementations, the techniques could include designating a volume of interest designated by a colored cursor for subsequent review. For medical images captured over time following an injection of any contrast material, color may be used to indicate presence and flow of the contrast material over time. Options include: combining the traces from the multiple images to show the blood vessel structure through which the contrast material moved; providing, at direction of the radiologist, time tags at point(s) of furthest movement of contrast material along each of the blood vessel's paths at each time interval; highlighting by color any connected blood vessels wherein no contrast has flowed as a potential indicator of blockage; and calculating, at direction of the radiologist, the volume of blood by time period for designated blood vessel(s) and display. In some implementations, the techniques could include for cases wherein there have been multiple sets of medical images taken over different time periods and for which a 3D volume of a tissue mass of interest has been recorded, providing the following: registration of the two (or more) volumes using the same metric system; superimposing the volumes and highlight by color (or other means such as flashing) the volumetric differences; and providing a histogram of volume of tissue of interest to quantify changes in size of the different tissue(s) within the cursor at the different times of imaging.

Referring to FIG. 5, another aspect of voxel adjustments based on radiodensity is enhanced voxel discrimination. The illustrated table 500 includes multipliers that enhance discrimination between voxels having near, but different, radiodensity and grayscale values. Voxels with Hounsfeld units of measure 25 (and associated grayscale) are multiplied by 1.2; voxels with Houndsfeld units of 30 (and associated grayscale) are multiplied by 1.5; voxels with Houndsfeld units of 35 (and associated grayscale) are multiplied by 2.0. Any of a wide variety of mathematical adjustments could be used, e.g. the table could be additive instead of multiplicative. Variations may include application of linear or non-linear functions. For example, the linear function (mX+b) could have the variable 'm' (i.e., slope) adjusted from a low slope to a higher slope. The non-linear function could be parabolic ($aX^2+bX+c$) (or other) where X would be the original grayscale. For other implementations, there could be a step increase. This is one of several ways to increase the ability to visually perceive small differences in radiodensity by adjusting the corresponding grayscale values, thereby improving visualization of the anatomy.

The mathematical adjustments may be temporally adjusted in response to controller-entered commands. The illustrated example includes three temporal multiplier adjustments that are iterated. In some implementations, if filtering results in display of a fraction/percent of the voxels, then the display could alternate display of voxels not currently to be displayed at selected time intervals. In some implementations, color could be added, such as rainbow, to particular ranges to enhance visibility.

Figure 6:
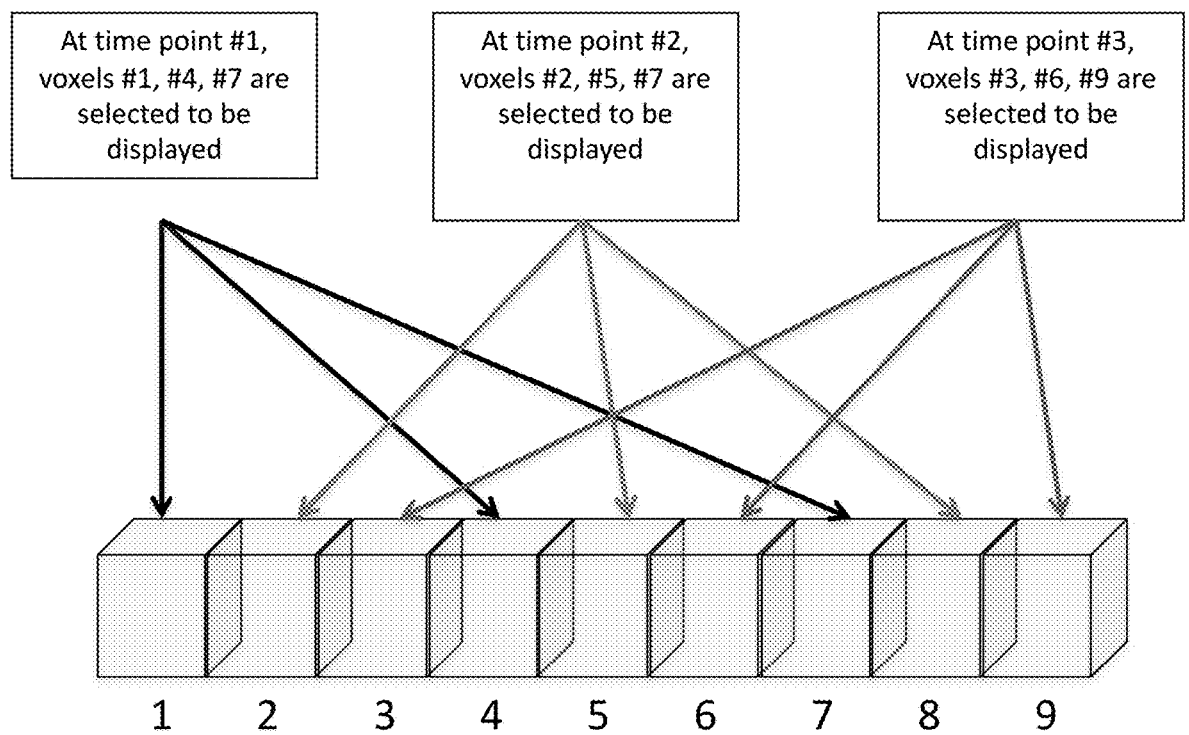
FIG. 6 illustrates aspects of filtering in greater detail.

FIG. 6 illustrates aspects of filtering in greater detail. In the illustrated example the filter is configured to select ⅓rd of the voxels for display at a given time. Specifically, every third voxel in a row of nine voxels numbered 1 through 9 is selected. Further, the filter temporally adjusts which ⅓rd of the voxels is selected for display at time points #1, #2, and #3 such that different sets of voxels are selected for display at different points in time. It may be advantageous to display only a portion of the voxels that represent a particular feature or tissue, e.g., air or fat. In the illustrated example only ⅓rd of the voxels of a certain radiodensity, and thus grayscale value, are shown at any one time. This option could also alternate which ⅓rd would be displayed over time. Note that the ⅓rd would not be a fixed fraction but one that was selectable.

Figure 7:
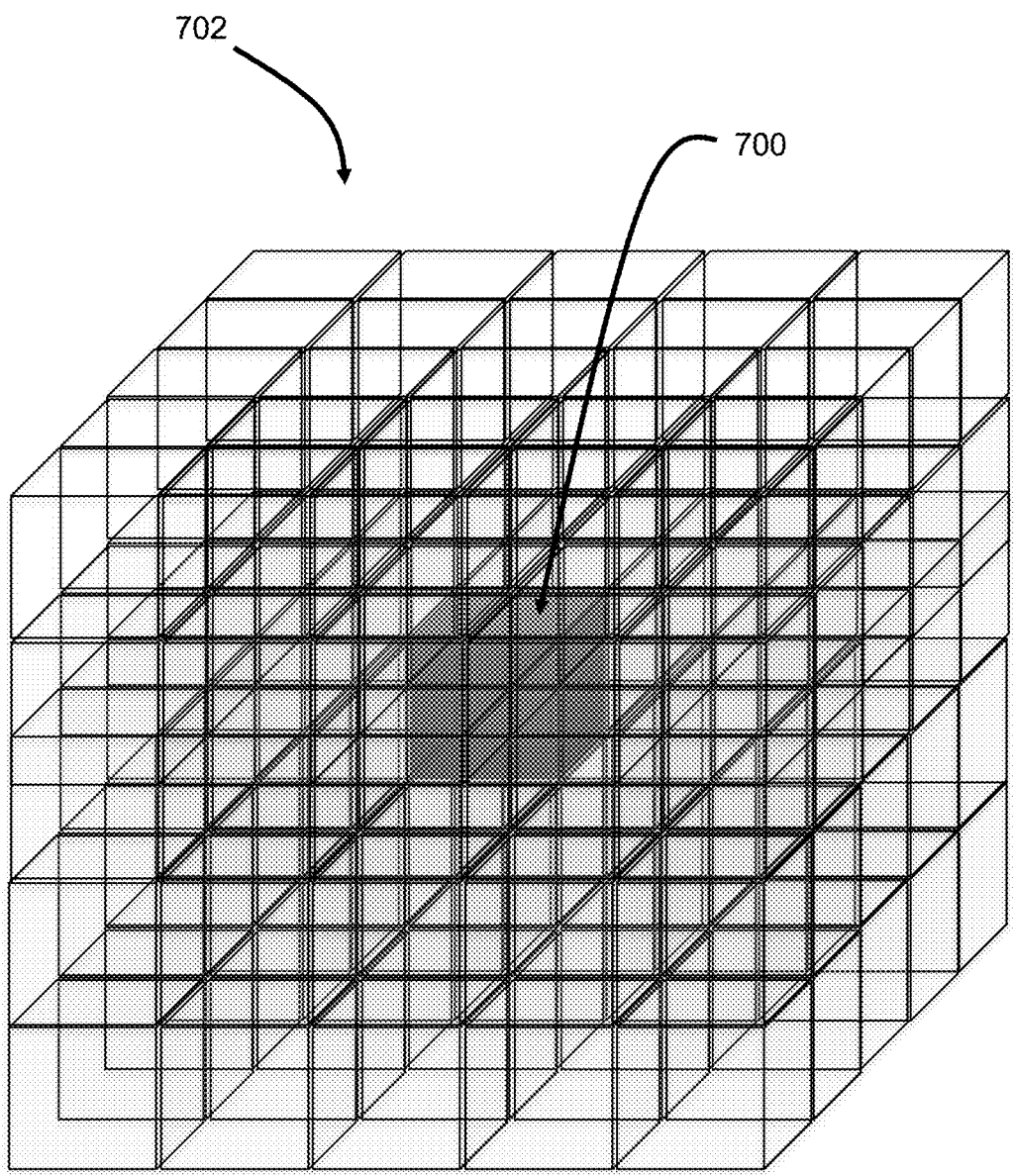
FIG. 7 illustrates an aspect of segmentation in which a voxel is classified based on the type of tissue of its nearest neighbor voxels.

FIG. 7 illustrates an aspect of segmentation in greater detail. In the illustrated example the tissue type of a voxel 700 under consideration is classified based on the tissue type of nearest neighbor voxels in a matrix. Although a 5×5×5 matrix 702 is shown, matrices of other sizes may be used, or adjacent voxels may be considered as nearest neighbors. Moreover, the set or matrix of voxels is not necessarily arranged in a cube. The 124 nearest neighbor voxels in the 5×5×5 matrix 702 are already classified with the same tissue type, so voxel 700 is likewise classified. Selection and configuration of segmentation algorithms would be via a controller at the discretion of the medical personnel viewing the images.

Figure 8A:
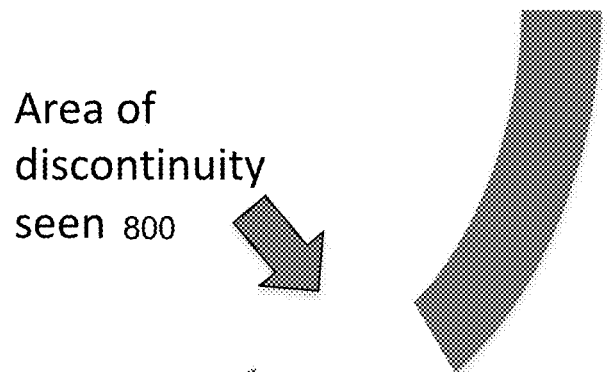
FIGS. 8A and 8B illustrate aspects of advanced segmentation wherein gaps in a vascular structure are filled.
Figure 8B:
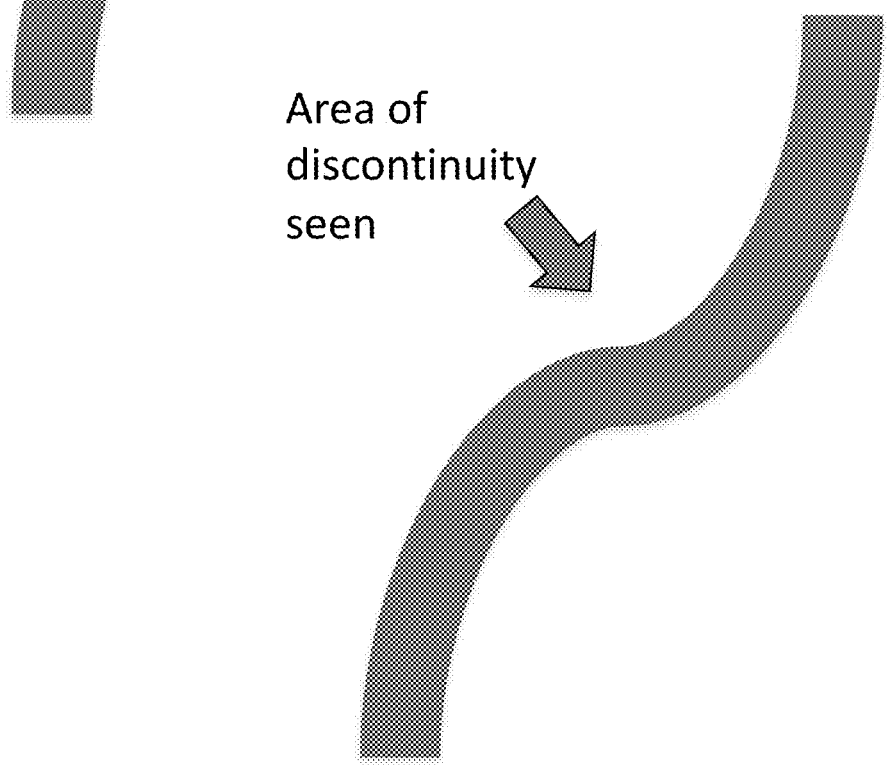

FIGS. 8A and 8B illustrate another aspect of segmentation. In the illustrated example, a gap 800 in a vascular structure is filled. There can be instances where a portion of certain connected tissue is not properly segmented when 2D algorithms are applied to 3D medical images. Vascular structure presents key challenges due to its curved nature within the body; it does not necessarily conform with a 3D grid structure. Advanced segmentation algorithms can be applied to grow the vascular structure from what is shown in FIG. 8A to what is shown in FIG. 8B. Selection of whether to apply advanced segmentation algorithms would be via a controller at the discretion of the medical personnel viewing the images.

Figure 9:
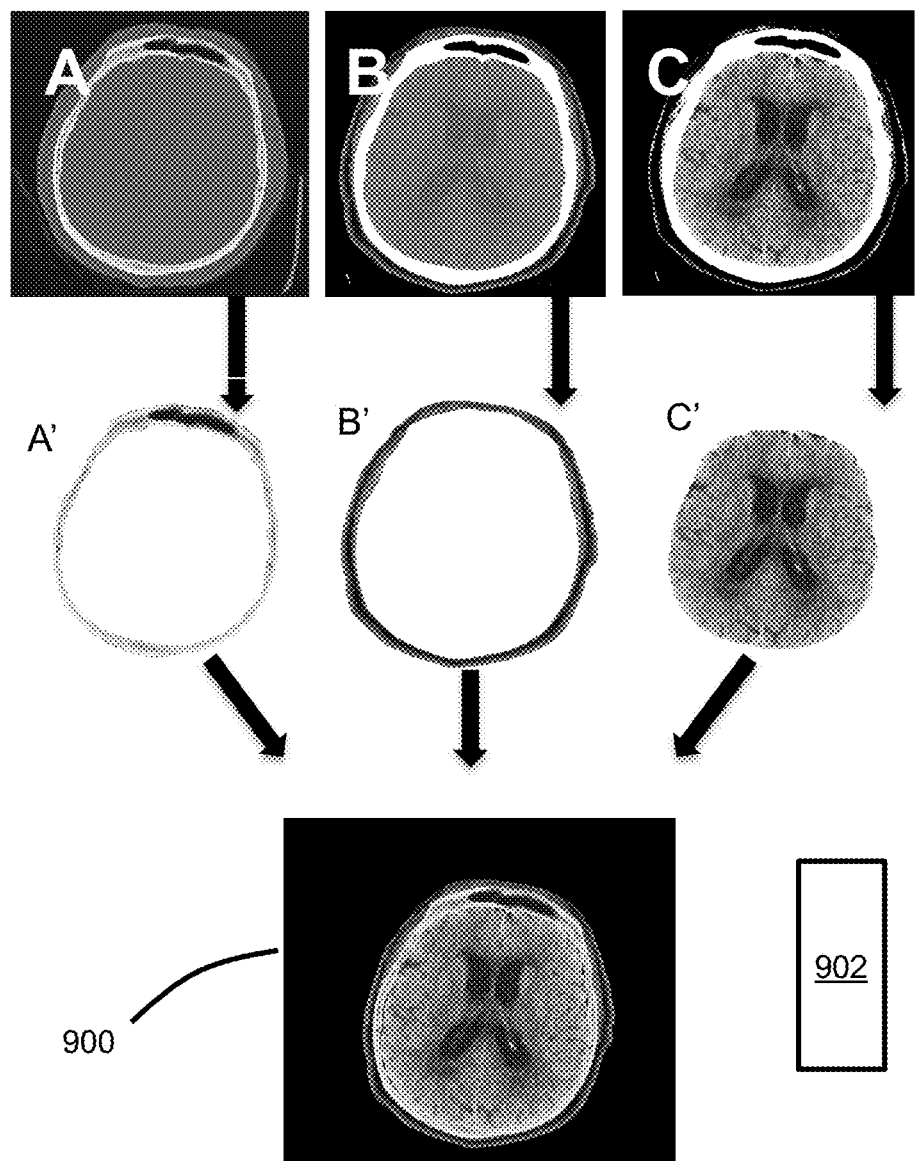
FIG. 9 illustrates use of controller-entered commands to process and combine three axial CT images of the head using the described image processing techniques.

FIG. 9 illustrates use of controller-entered commands and image processing logic to generate three axial CT images of the head and combine features extracted therefrom to generate a composite image. Images A, B, and C are generated with any combination of the image processing techniques described above. Bone algorithm image A demonstrates optimal visualization of the calvarium. Grayscale level adjustments based on radiodensity have been configured to optimize visualization of the cancellous bone within the calvarium (window level of 360 and window width of 3400). A side-effect is poor visualization of the scalp and almost no detail of the brain. The brain tissue cannot even be distinguished from the cerebrospinal fluid (CSF). Soft tissue algorithm image B is generated from the same raw image data by grayscale level adjustments based on radiodensity to optimize visualization of the scalp (window level of 40 and window width of 350). Soft tissue algorithm image C is generated from the same raw image data by grayscale level adjustments based on radiodensity to optimize visualization of the brain (window level of 30 and window width of 100).

The features of interest that have been visually optimized in images A, B, and C may be selected and extracted to generate a corresponding set of extracted feature images A', B', and C'. The extracted feature images may then be combined to generate a composite image 900. In the illustrated example, each extracted feature image includes unique tissue or tissues within the set of extracted feature images so there is no overlap when the three extracted feature images are combined to generate the composite image that represents all tissues. However, overlapping voxels having different values could be resolved algorithmically. Advantageously, the image processing steps are efficiently implemented in response to controller-entered commands based on a visual/graphical interface, e.g. via the VR headset.

Another aspect of visualization is the capability to combine findings with structured reporting. In some implementations, this could include displaying a list 902 of items which could be digitally marked by the radiologist using the 3D controller. The list of items could be unique to each item on the radiologist review checklist. In some implementations, the list presented on the 3D head display unit or the 2D display. Items which had been digitally marked would be automatically included in the report. In some implementations, a list of frequently used phrases for each item on the radiologist review checklist could be displayed at the direction of the radiologist who could then digitally mark any of the relevant phrases. Phrases which had been digitally marked would be automatically included in the report.

Another aspect of visualization is changing viewing perspective. In some implementations, a selected image, volume, feature, tissue, voxel set, or voxel is automatically re-centered or re-located to enhance radiologist orientation of location within the volume being examined. Examples of auto re-location include, but are not limited to, the following: the viewing perspective could be re-located to an initial viewing point of an image set; and the viewing perspective could be re-located to additional point(s) designated by the radiologist during the course of the examination. In some implementations, the cursor color or shape could correspond to pre-selected conditions, for example, but not limited to: review checklist items; types of tissue of concern; and regions for collaboration between medical personnel.

Another aspect of visualization is the capability to switch between various dimensional views (i.e., change back and forth between viewing 3D volume and 2D slices). In some implementations, selection of the 2D slice could be based on, but not limited to: the center point of the 3D cursor; a point within the 3D volume designated by the radiologist. In some implementations, the 3D controller to scroll through the slices.

Figure 10:
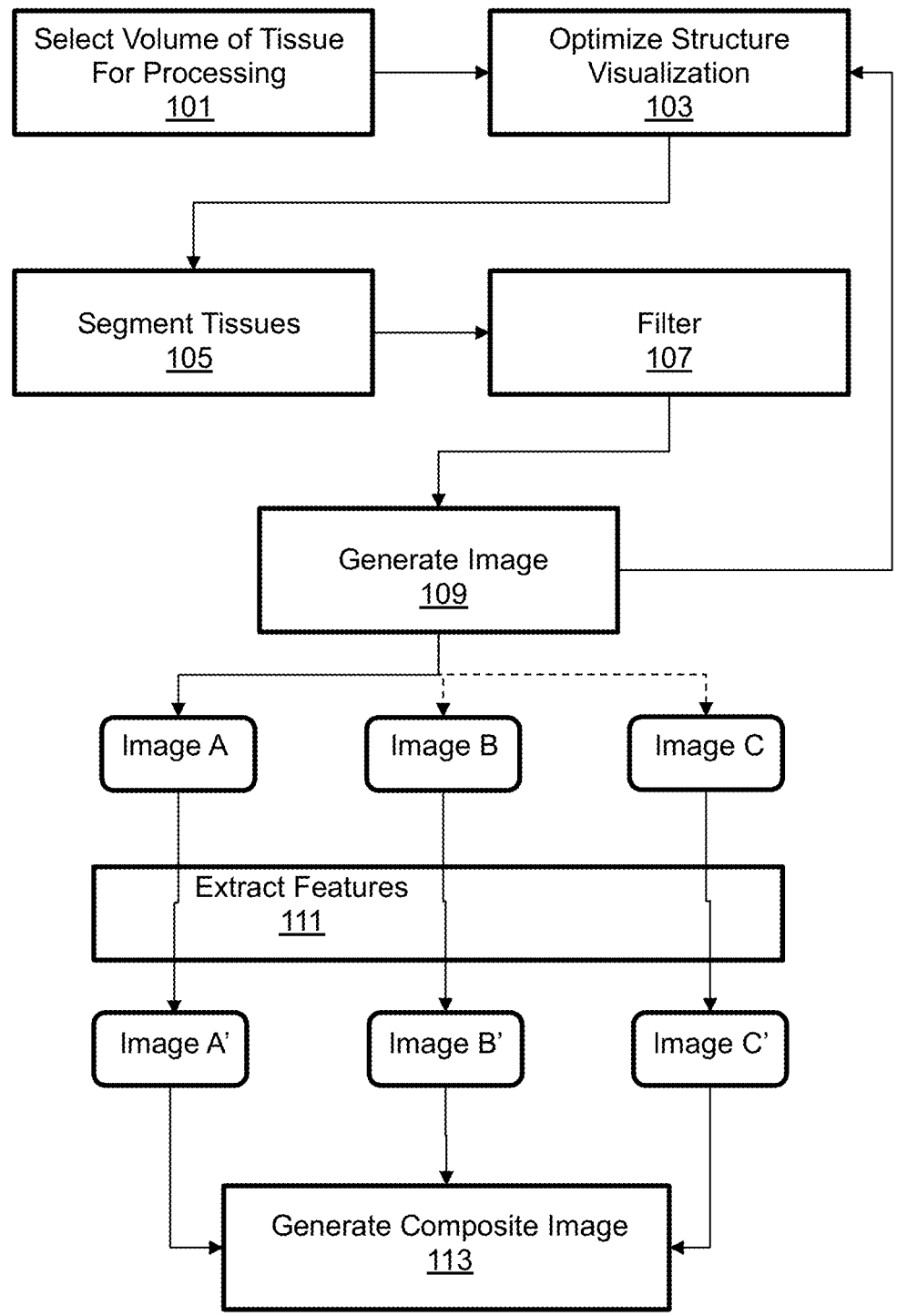
FIG. 10 is a flow diagram of procedural steps in accordance with aspects of the invention.

FIG. 10 illustrates a method in accordance with aspects of the invention. Procedurally, a volume of tissue within the body may initially be selected for processing in step 101. Raw scan data is retrieved for the selected volume, and one or more processing algorithms may be selected, configured, and applied. For example, one or more voxels adjustments based on radiodensity may be implemented to enhance one or more features of interest and optimize structure visualization as shown in step 103. Further, one or more segmentation algorithms may be selected, configured, and applied to segment tissues as shown in step 105. Further, filters may be selected, configured, and applied as shown in step 107. An image A is then generated based on the processing algorithms as shown in step 109. Steps 103, 105, 107, and 109 may be iterated for the selected volume any number of times to generate more images, e.g. images that enhance different tissues or features within the selected volume. In the illustrated example image B and image C are generated with different processing algorithms and/or configuration settings. The enhanced tissues or features from the images A, B, C are then extracted as shown in step 111, resulting in extracted feature images A', B', and C'. The extracted feature images are then combined to generate a composite image as shown in step 113.

FIG. 11 illustrates optimal viewing settings for 2D imaging and for 3D imaging. A list of the optimal viewing settings is generated for each item in an image. In 1100, two examples are provided within an image are shown along with the optimal viewing settings during 2D slice-by-slice viewing per user preference. In the first example, the liver is viewed on a CT scan with conventional settings. The liver is shaded in gray shades and with particular group (e.g., specified range is designed to catch hypervascular tumors, necrotic tumors, etc.) in color with option for voxel manipulation. All other tissues are turned to dark gray shades. In the second example, the breast is viewed during a digital breast tomosynthesis examination. Breast glandular parenchyma in gray shades with particular s (e.g., specified range is designed to catch microcalcifications) shown in red. Additionally, as discussed elsewhere in this disclosure and in U.S. patent application Ser. No. 16/195,251, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION, the voxels are can be manipulated. This can be utilized to improve visualization. In 1102, a first visual representation adjustment logic is applied to the entire image, such as performing a liver window wherein voxels whose Hounsfield units are less than −45 are black, voxels whose Hounsfield units are more than +105 are white and voxels whose Hounsfield units are shades of gray. Additionally, this embodiment also enables a second visual representation adjustment logic to be applied to voxels whose range is in between +80 to +105. This "group" helps the user pick out hypervascular liver metastases whose density is typically in the range of +80 to +105, as shown in red. The preferred embodiment is for the technique to be performed in conjunction with segmentation (e.g., segment the organ and then apply the described visual representation adjustment logic); however, this would not necessarily be required. Additionally, this embodiment also enables a third (or more) visual representation adjustment logic to be applied, such as coloring a group of voxels in the range of +20 to +30 would be in the range of necrotic liver tumors the color green. In 1104, two items within an image are shown along with the optimal viewing settings during 3D extended reality volume-by-volume viewing per user preference. For example, prioritized volume rendering of HU ranges is utilized within the liver and displayed in a dynamic fashion to make more subtle (but dangerous lesions) easier to detect. This is described in more detail in U.S. Provisional Patent Application No. 62/846,770, A method of prioritized volume rendering to improve visualization of prioritized items within a 3D volume. Additionally, the voxels that subtend the liver are divided into groups based on their property (e.g., Hounsfield Unit). For example, assume that voxels that subtend the liver have Hounsfield of 30-60. These can be divided into 3 groups (e.g., upper range of 50-60 HU, a middle range of 40-50 HU, and a lower range of 30-40 HU) wherein at three different time points one of the groups has enhanced visualization (e.g., color schemes) and the other two groups have diminished visualization (e.g., dark gray scale). This process wherein voxels are divided into groups and then visualization enhanced or diminished improves detection of subtle lesions. For example, the liver parenchyma should appear homogeneous on each of the 3 phases. Peering into the liver at each phase can help a certain masses that tend to fall in a band stand out from the rest of the liver parenchyma. All other tissues are made more translucent (e.g., sparse sampling) or are filtered. For example, for prioritized volume rendering is performed wherein voxels with higher priority and be displayed. All other tissues are made more translucent (e.g., via sparse sampling) or are filtered. This processed may be performed in accordance with a checklist.

Figure 12:
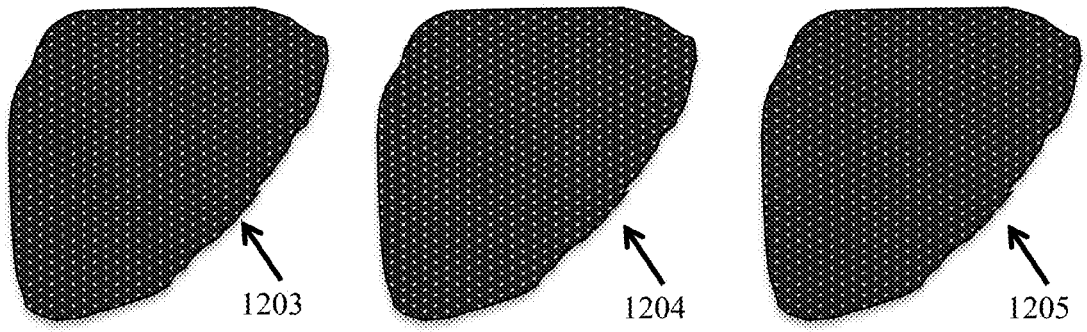
FIG. 12 illustrates utilization of range-based grouping as a display settings.

FIG. 12 illustrates utilization of range-based grouping as a display settings. Certain voxels within the liver having improved visualization through group-wise visual representation adjustment logic. In this embodiment, voxels are first divided into groups and then visual representation adjustment logic is applied wherein at least one group of voxels has a different visual representation adjustment logic as compared to at least one other group of voxels. For example, consider the liver. Assume that the liver is segmented and inside the segmented liver are voxels with Hounsfield Units ranging between 30-60. This embodiment improves visualization and inspection of liver (HU of 30-60) by dividing the voxels into groups (e.g., upper range of 50-60 HU, a middle range of 40-50 HU, and a lower range of 30-40 HU). Then, at three different time points one of the groups has enhanced visualization (e.g., rainbow color, midgray to white shades only, etc.) and the other two groups have diminished visualization (e.g., dark grayscale). Through user inputs, the first group (e.g., upper group with range of 50-60 HU) would be optimally displayed during the first time period and the middle and lower groups would have diminished visualization. In this illustration, the optimized group during the first time period has HU of 50-60 and is assigned yellow shades and the remainder of the groups (HU 30-50) have diminished visualization and are assigned dark gray to black shades. Then, through user inputs (or via automated process) the second group (e.g., middle group with range of 40-50 HU) would be optimally displayed during the second time period and the highest group (e.g., HU 50-60) and lowest group (e.g., HU 30-40) would have diminished visualization. In this illustration, the optimized group during the second time period has HU of 40-50 and is assigned light green shades and the remainder of the groups (HU 30-40 and HU 50-60) have diminished visualization and are assigned dark gray to black shades. Finally, through user inputs (or via an automated process) the third group (e.g., lower group with range of 30-40 HU) would have optimized visualization and the upper (e.g., HU 50-60) and middle groups (e.g., HU 40-50) would have diminished visualization. In this illustration, the optimized group during the third time period has HU of 30-40 and is assigned light purple shades and the remainder of the groups (HU 40-60) have diminished visualization and are assigned dark gray to black shades. This process of changing the appearance could be performed on 2D slices on a radiology monitor. Alternatively, it could be performed on 3D volumes using augmented reality, mixed reality or virtual reality displays and groups selected for diminished visualization would be preferentially filtered. Given that the groups that are filtered change over time (e.g., per user preference), then this filtering would be dynamic. This process wherein voxels are divided into groups and then visualization enhanced or diminished improves detection of subtle lesions. 1202 illustrates a text box, which states range grouping prior to implementing visual representation adjustment logic. 1203 is the liver at a first time point. 1204 is the liver at a second time point. 1205 is the liver at a third time point. The text box 1206 illustrates at time point 1 that the optimized band has Hounsfield Units of 50-60 and is shown in yellow shades and the diminished band has Hounsfield Units of 30-50 and is shown in dark gray to black shades. The text box 1207 illustrates at time point 2 that the optimized band has Hounsfield Units of 40-50 and is shown in light green shades and the diminished band has Hounsfield Units of 30-40 and 50-60 and is shown in dark gray to black shades. The text box 1208 illustrates at time point 3 that the optimized band has Hounsfield Units of 30-40 and is shown in light purple shades and the diminished band has Hounsfield Units of 40-60 and is shown in dark gray to black shades.

FIG. 13 illustrates generating multiple simultaneous window/level settings for viewing of 3D datasets. Step 1300 illustrates performing a first windowing and leveling setting. Step 1301 illustrates performing segmentation of organs. 1302 illustrates generating a list of data that might be normal vs. abnormal. 1303 illustrates applying a first visual representation adjustment logic to standard window/level setting to voxels that are thought to be normal. 1304 illustrates applying second visual representation adjustment logic (false color) that are thought to be abnormal. 1305 illustrates an option to apply additional (third or more) visual representation adjustment logic to additional ranges.

Figure 14:
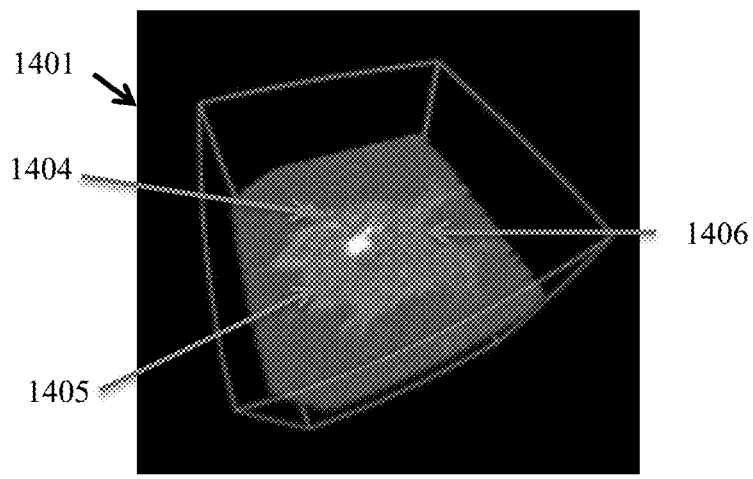
FIG. 14 illustrates challenges faced of visualizing certain ranges without multiple windowing.

FIG. 14 illustrates challenges faced of visualizing certain ranges without multiple windowing. 1400 is a text box which provides description of the dataset. The following image is a sub-volume of a CT scan of the breast, inside of a volume-subtending 3D cursor. The sub-volume is comprised of approximately 100×100×100 or 1 million voxels. 1401 illustrates an image of the sub-volume. 1404 illustrates a first voxel that blends in with the rest of the gray shades. 1405 illustrates a second voxel that blends in with the rest of the gray shades. 1406 illustrates a third voxel that blends in with the rest of the gray shades. 1407 illustrates a text box, which states an embodiment of this patent is to be able to improve imaging by making some voxels (e.g., voxels with Hounsfield Unit range 70-75) to have a "special" visibility.

FIG. 15 illustrates with overcoming challenges in visualizing certain ranges when using viewing multiple windowing. 1500 is a text box. Step #1 is to divide the voxels into ranges. The first range will include all voxels with Hounsfield Units between 70 and 75. Assume that there are 3 voxels in this first band. The second range will include all other voxels in the volume. Assuming the 100×100×100 matrix, that would equal 999,997 voxels in this second band. Step #2 is to assign visual representation adjustment logic to the first band of 3 voxels (e.g., color all voxels in this band yellow). Step #3 is to assign a different visual representation adjustment logic to the second band of 999,997 voxels (e.g., color voxels in this band varying shades of gray based on Hounsfield Units and conventional windowing and leveling settings. 1501 shows that the first voxel has been re-assigned a yellow color, from its previous gray-scale appearance. 1502 shows that the second voxel has been re-assigned a yellow color, from its previous gray-scale appearance. 1503 shows that the third voxel has been re-assigned a yellow color, from its previous gray-scale appearance.

FIG. 16 illustrates a method of improving image quality. Step 1600 is to perform imaging examination. Step 1601 is to load an original imaging dataset of a patient wherein each pixel or voxel within the imaging dataset has an associated data unit. Step 1602 is to perform segmentation of the imaging dataset (e.g., segment a phantom, segment the anatomy, segment structures outside of the patient, etc.). Step 1603 is to select a first segmented structure for analysis. Step 1604 is to perform at least one measurement of the data unit(s) within the first segmented structure. Step 1605 is to determine the expected value(s) of the data unit(s) within the first segmented structure. Step 1606 is to determine at least one correction factor based on the difference between the at least one measurement(s) of the data unit(s) within the first segmented structure and the expected value(s) of the data unit(s) within the first segmented structure wherein the corrective factor can be applied to a second segmented structure to cause improved image quality. Step 1607 is to input the at least one corrective factor to modify the data units of at least one of the group comprising the first segmented structure and the second segmented structure in the original imaging dataset to create a modified imaging dataset wherein the modified imaging dataset has improved image quality.

Figure 17:
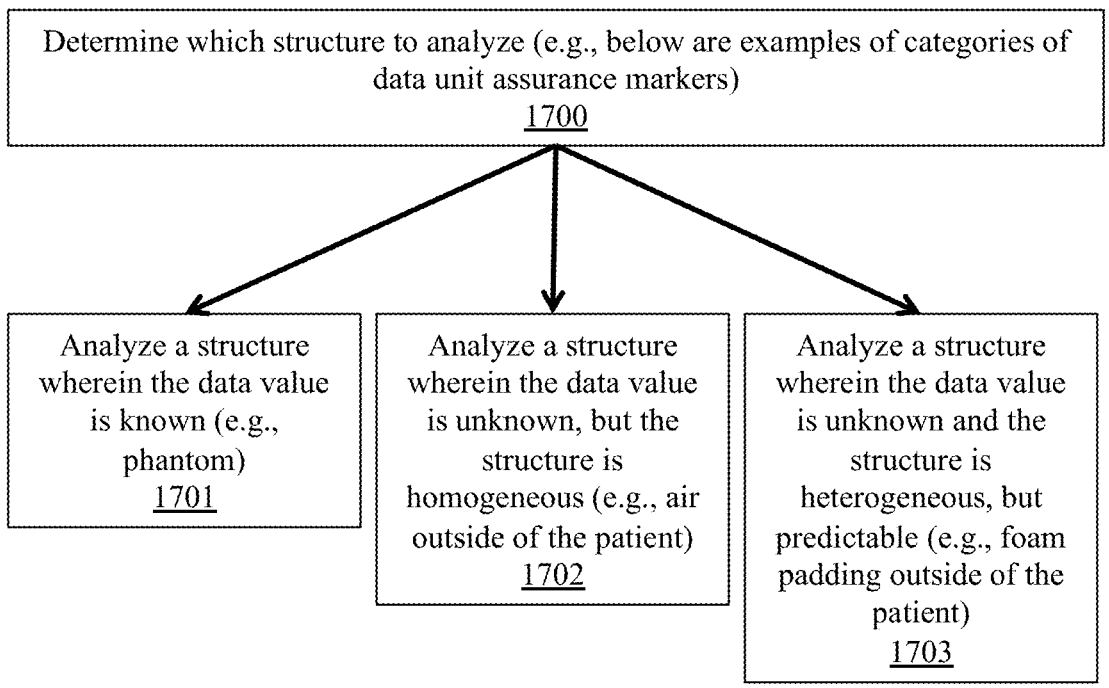
FIG. 17 illustrates a method of identifying data unit assurance markers.

FIG. 17 illustrates a method of identifying data unit assurance markers. This also provides identifying which structure can be analyzed. Step 1700 is to determine which structure to analyze (e.g., below are examples of categories of data unit assurance markers). A first suggested option 1701 is to analyze a structure wherein the data value is known (e.g., phantom). A second suggested option 1702 is to analyze a structure wherein the data value is unknown, but the structure is homogeneous (e.g., air outside of the patient). A third suggested option 1703 is to analyze a structure wherein the data value is unknown and the structure is heterogeneous, but predictable (e.g., foam padding outside of the patient).

Figure 18:
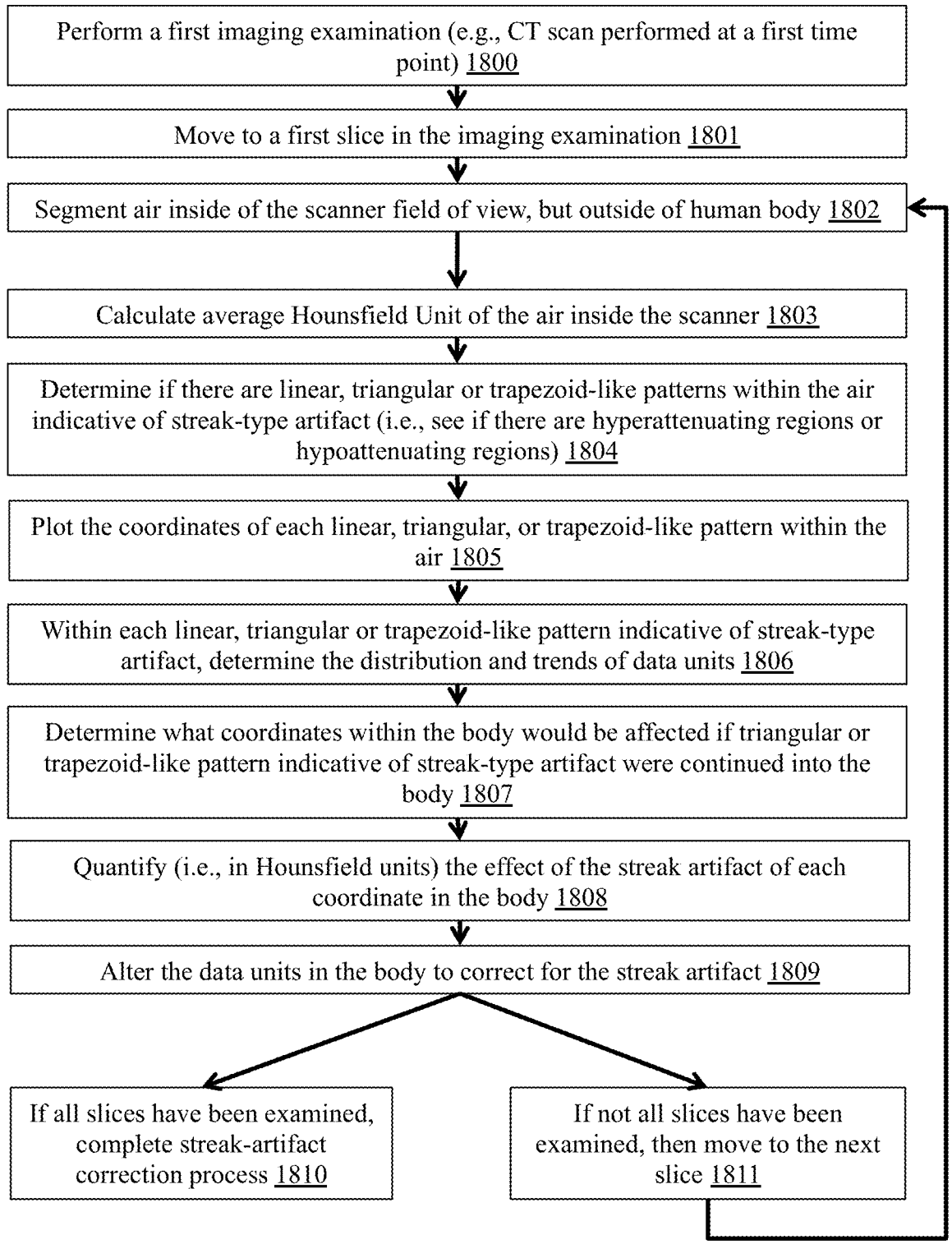
FIG. 18 illustrates an example of analyzing density of air outside of the patient's body to correct for artifacts within the patient's body.

FIG. 18 illustrates an example of analyzing density of air outside of the patient's body to correct for artifacts within the patient's body. Step 1800 is to perform a first imaging examination (e.g., CT scan performed at a first time point). Step 1801 is to move to a first slice in the imaging examination. Step 1802 is to segment air inside of the scanner field of view, but outside of human body. Step 1803 is to calculate average Hounsfield Unit of the air inside the scanner. Step 1804 is to determine if there are linear, triangular or trapezoid-like patterns within the air indicative of streak-type artifact (i.e., see if there are hyperattenuating regions or hypoattenuating regions). Step 1805 is to plot the coordinates of each linear, triangular, or trapezoid-like pattern within the air. Step 1806 is to within each linear, triangular or trapezoid-like pattern indicative of streak-type artifact, determine the distribution and trends of data units. Step 1807 is to determine what coordinates within the body would be affected if triangular or trapezoid-like pattern indicative of streak-type artifact were continued into the body. Step 1808 is to quantify (i.e., in Hounsfield units) the effect of the streak artifact of each coordinate in the body. Step 1809 is to alter the data units in the body to correct for the streak artifact. Note that this could be done for many different types of artifact in both CT and MRI. Step 1810 is if all slices have been examined, complete streak-artifact correction process. Step 1811 is if not all slices have been examined, then move to the next slice and return to step 1802. Nested do loops and other types of software strategies can be performed to accomplish these type steps.

FIG. 19A illustrates a CT image of the head with window and level settings optimized for visualization of air. Note that there are groups of high density and low density inside of the segmented air. These correspond to areas of streak artifact.

FIG. 19B illustrates a zoomed in CT image of the head with window and level settings optimized for visualization of air. Note that a trapezoid 1910 is shown in the image to denote the dark group.

FIG. 19C illustrates a plot of voxels within the region of air, which can be used to determine the correction factor applied to voxels within the head. 1901 illustrates a trapezoid containing voxels inside of the head. 1900 illustrates a trapezoid containing voxels in the air outside of the head. Voxel 1902 is shown farthest away from the scalp and has a Hounsfield Unit of −987. Voxel 1903 is mid-way from the scalp and has a Hounsfield Unit of −976. Voxel 1904 is closest to the scalp and has a Hounsfield Unit of −951. Voxel 1905 is in the superficial scalp and has a Hounsfield Unit of −103. Voxel 1906 is in the brain and has a Hounsfield Unit of 24. A correction factor is applied. Voxel 1902 is corrected to −1000. Voxel 1903 is corrected to −1000. Voxel 1904 is corrected to −1000. Voxel 1905 is corrected to −90. Voxel 1906 is corrected to 30.

Figure 20:
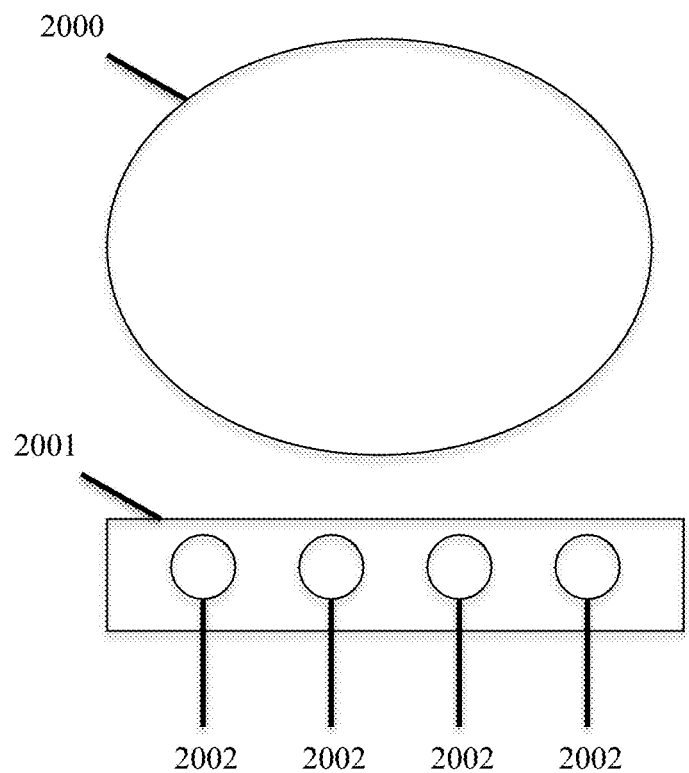
FIG. 20 illustrates an example of placing phantoms inside of a table associated with a scanner.

FIG. 20 illustrates an example of placing phantoms inside of a table associated with a scanner. The patient 2000 is shown. The table 2001 is shown. Multiple phantoms 2002 are shown. The type of phantoms used can vary greatly (e.g., designed with varying size, materials, and locations). The design may also vary based on the type of examination and the indication of the examination.

Figure 21:
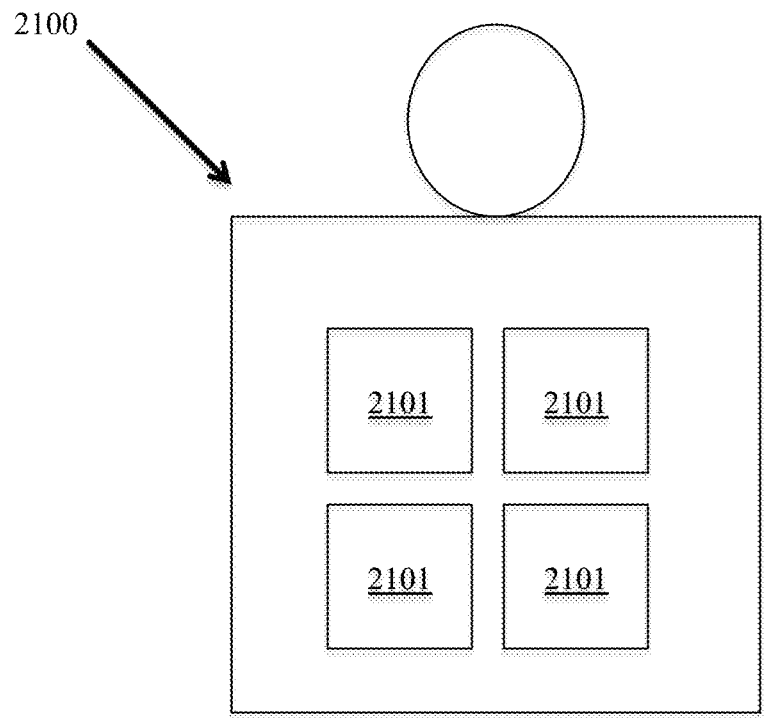
FIG. 21 illustrates an example of placing phantoms onto the patient.

FIG. 21 illustrates an example of placing phantoms onto the patient. The patient 2100 is shown. Multiple phantoms 2101 are shown on the patient. Note that the phantoms could also be inside of the patient, preferably in the form of ingested capsules wherein each capsule contains at least one substance (e.g., water, oils, etc.). This would serve as internal landmarks. Other implantable phantoms (e.g., via surgery or needle placement) could be performed for certain conditions that require precision monitoring (e.g., brain tumor signal). The implantable phantoms may also be placed onto or within a variety of surgical devices (e.g., pacemaker, port-a-cath, etc.).

Figure 22:
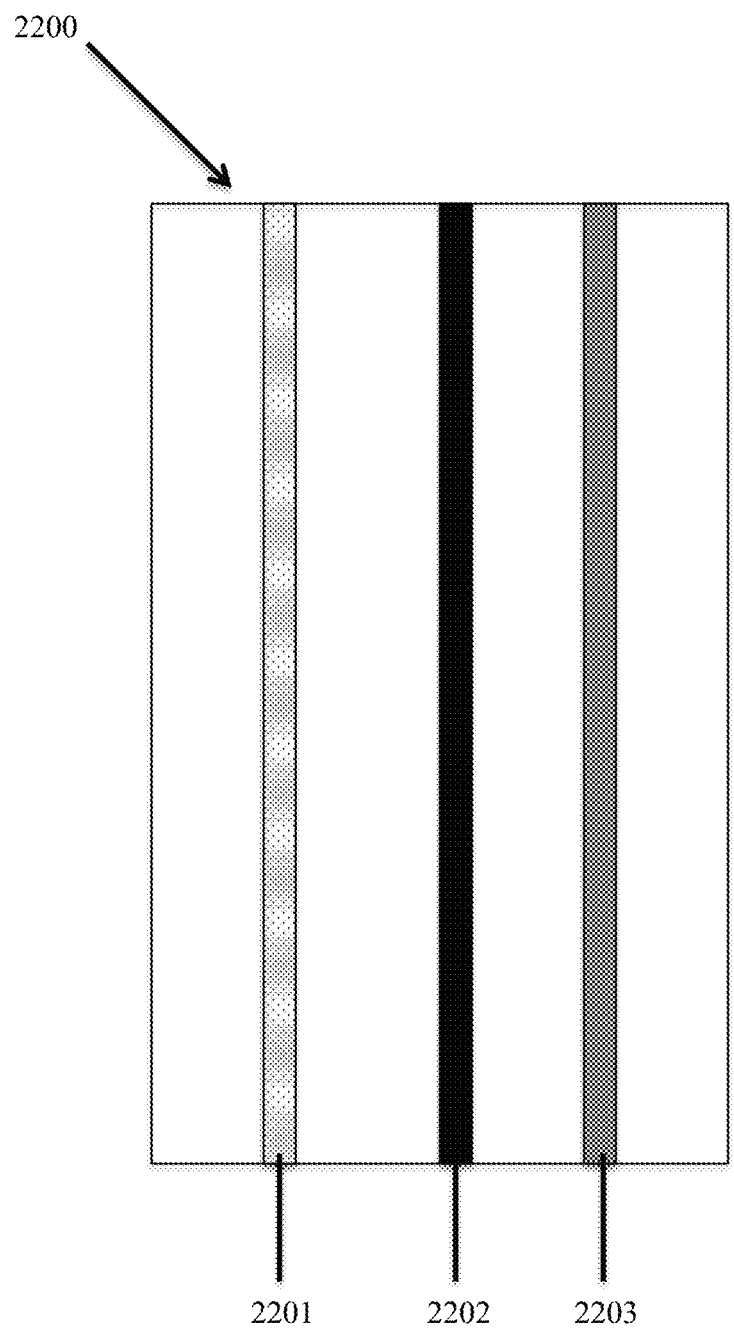
FIG. 22 illustrates an example of placing phantoms onto a blanket.

FIG. 22 illustrates an example of placing phantoms onto a blanket. The blanket 2200 is shown. A first material 2201 is shown in the blanket. A second material 2202 is shown in the blanket. A third material 2203 is shown in the blanket. This could be used to wrap the patient and improve reliability of the data units of a particular examination.

Figure 23A:
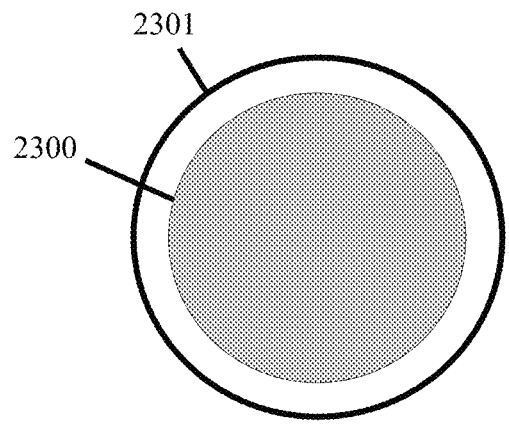
FIG. 23A illustrates a phantoms surrounding a patient in a single, circumferential layer.

FIG. 23A illustrates a phantoms surrounding a patient in a single, circumferential layer. 2300 is the patient. 2301 is the single, circumferential layer of phantoms. Based on the measured signal in the phantom, corrections to the dataset can be made.

Figure 23B:
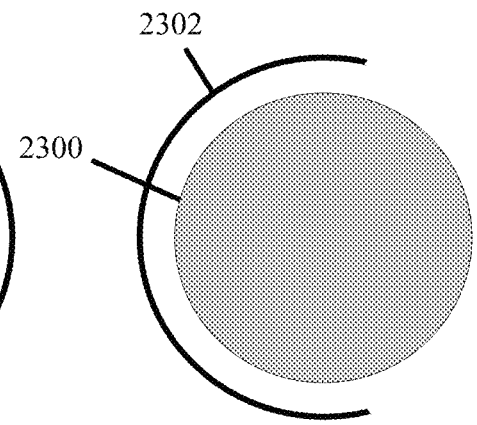
FIG. 23B illustrates a phantoms surrounding a patient in a single layer, which is not circumferential.

FIG. 23B illustrates a phantoms surrounding a patient in a single layer, which is not circumferential. 2300 is the patient. 2302 is the single, non-circumferential layer of phantoms. Based on the measured signal in the phantom, corrections to the dataset can be made.

Figure 23C:
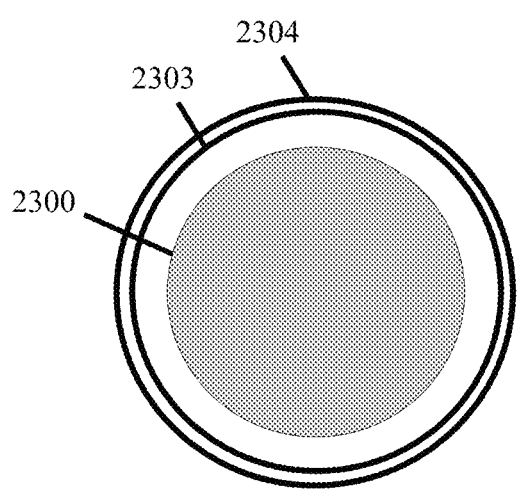
FIG. 23C illustrates a phantoms surrounding a patient multiple, circumferential layers.

FIG. 23C illustrates a phantoms surrounding a patient multiple, circumferential layers. 2300 is the patient. 2303 is the first layer of a circumferential layer of phantoms. 2304 is the second layer of a circumferential layer of phantoms. Based on the measured signal in the phantom, corrections to the dataset can be made.

Figure 23D:
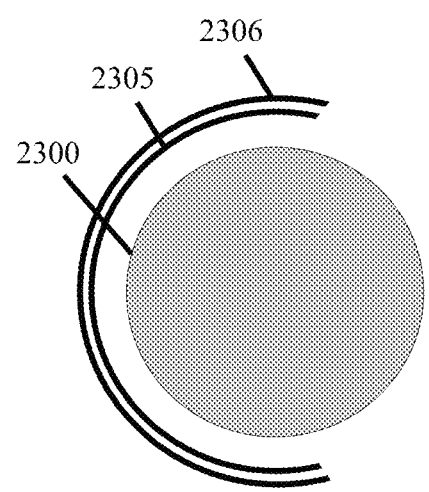
FIG. 23D illustrates a phantoms surrounding a patient in a multiple, non-circumferential layers.

FIG. 23D illustrates a phantoms surrounding a patient in a multiple, non-circumferential layers. 2303 is the first layer of a circumferential layer of phantoms. 2305 is the first layer of a non-circumferential layer of phantoms. 2306 is the second layer of a non-circumferential layer of phantoms. Based on the measured signal in the phantom, corrections to the dataset can be made. These examples are illustrative only. A wide variety of placement of phantoms could be performed in a scanner for data unit assurance purposes as described in this patent.

Figure 24:
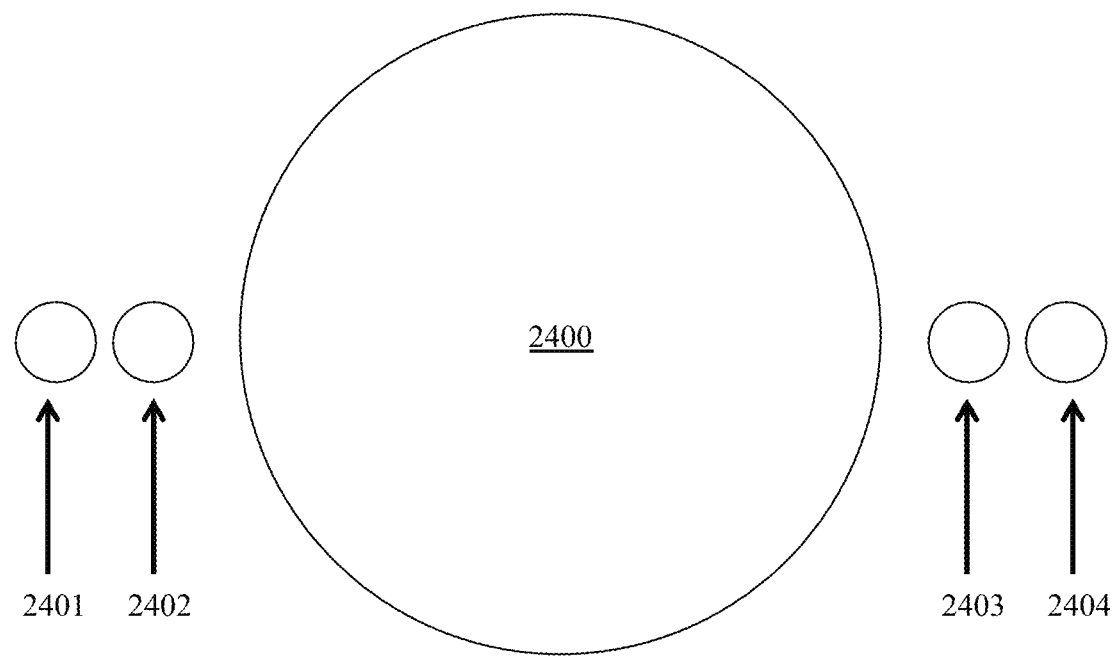
FIG. 24 illustrates multiple measurements in a radial fashion outward from the patient.

FIG. 24 illustrates multiple measurements in a radial fashion outward from the patient. This is an example of the phantom-based data unit correction. 2400 illustrates a cross-section of the patient. 2401 illustrates a first phantom, which contains only water. 2402 illustrates a second phantom, which contains only water. 2403 illustrates a third phantom, which contains only water. 2404 illustrates a fourth phantom, which contains only water. The preferred embodiment is multiple layers in the wrapping material, which allows factoring in differences in the data units over radial distance away from the patient. This provides increased accuracy.

Figure 25A:
FIG. 25A illustrates a region of streak artifact going from scalp soft tissue into the air.

FIG. 25A illustrates a region of streak artifact going from scalp soft tissue into the air. Note that the third row 2500 contains voxels measuring 40, 40, −990, −990, and −990. This third row 2500 illustrates streak artifact.

Figure 25B:
FIG. 25B illustrates the modified dataset wherein the streak artifact is corrected.

FIG. 25B illustrates the modified dataset wherein the streak artifact is corrected. Note that the third row 2501 contains voxels measuring 50, 50, −1000, −1000, and −1000. This third row 2500 illustrates correction of the streak artifact.

Figure 26:
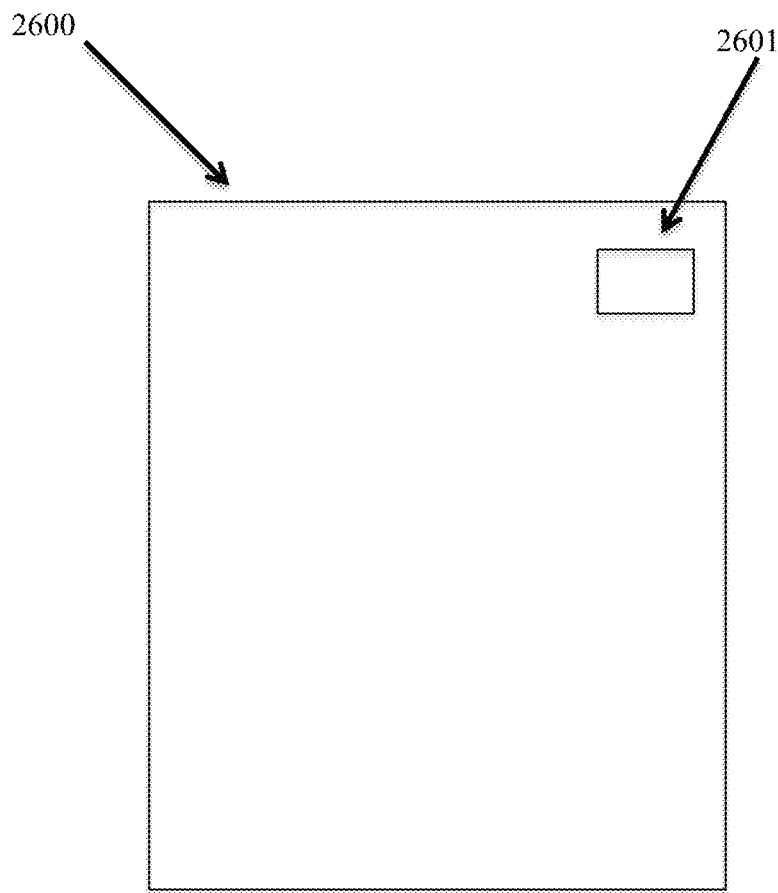
FIG. 26 illustrates an x-ray detector attached to a phantom.

FIG. 26 illustrates an x-ray detector attached to a phantom. 2600 is the x-ray detector. 2601 is the phantom. Please note that the number of phantoms, type(s) of phantoms and positions of phantoms can vary greatly.

Figure 27:
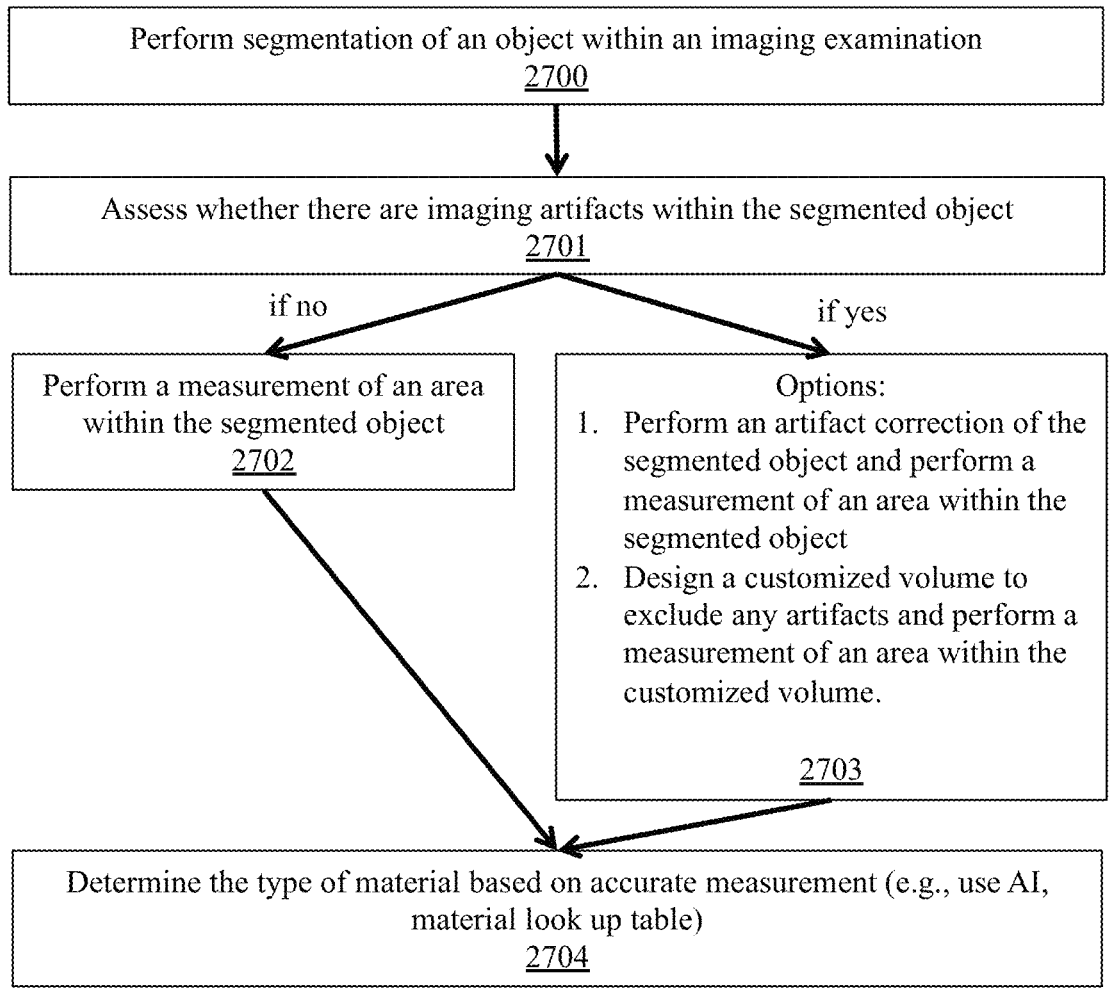
FIG. 27 illustrates a method of performing a precision estimate of a property of a material within an imaging examination.

FIG. 27 illustrates a method of performing a precision estimate of a property of a material within an imaging examination. 2700 illustrates performing segmentation of an object within an imaging examination. 2701 illustrates assessing whether there are imaging artifacts within the segmented object. If there are no imaging artifacts within the segmented object, then proceed to 2702, which is to perform a measurement of an area within the segmented object. If there are imaging artifacts within the segmented object, then proceed to 2703, wherein there are two options. First, perform an artifact correction of the segmented object and perform a measurement of an area within the segmented object. Second, design a customized volume to exclude any artifacts and perform a measurement of an area within the customized volume. 2704 illustrates determining the type of material based on accurate measurement. A first example would be to use lookup tables. A second example would be to use an artificial intelligence algorithm, which would use training data.

Figure 28A:
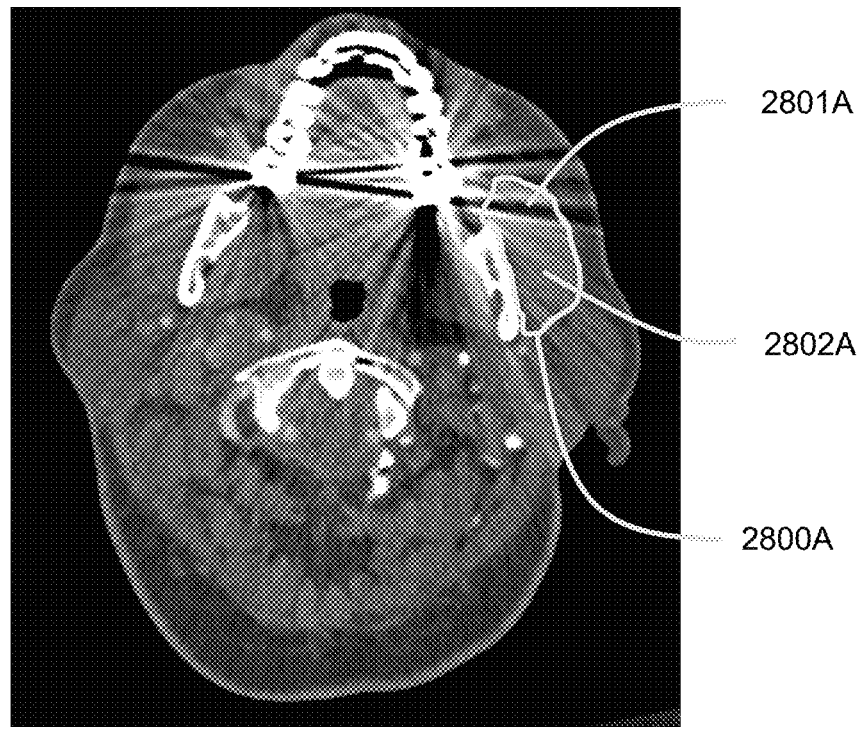
FIG. 28A illustrates an image of an object containing some areas whose data elements are inaccurate due to imaging artifacts and some areas whose data elements are accurate (i.e., not adversely affected by an imaging artifact).

FIG. 28A illustrates an image of an object containing some areas whose data elements are inaccurate due to imaging artifacts and some areas whose data elements are accurate (i.e., not adversely affected by an imaging artifact). 2800A illustrates segmentation to define the borders of the left masseter muscle. 2801A illustrates an area within the segmented masseter muscle adversely affected by streak artifact by CT. 2802A illustrates an area within the segmented masseter muscle not adversely affected by an imaging artifact.

Figure 28B:
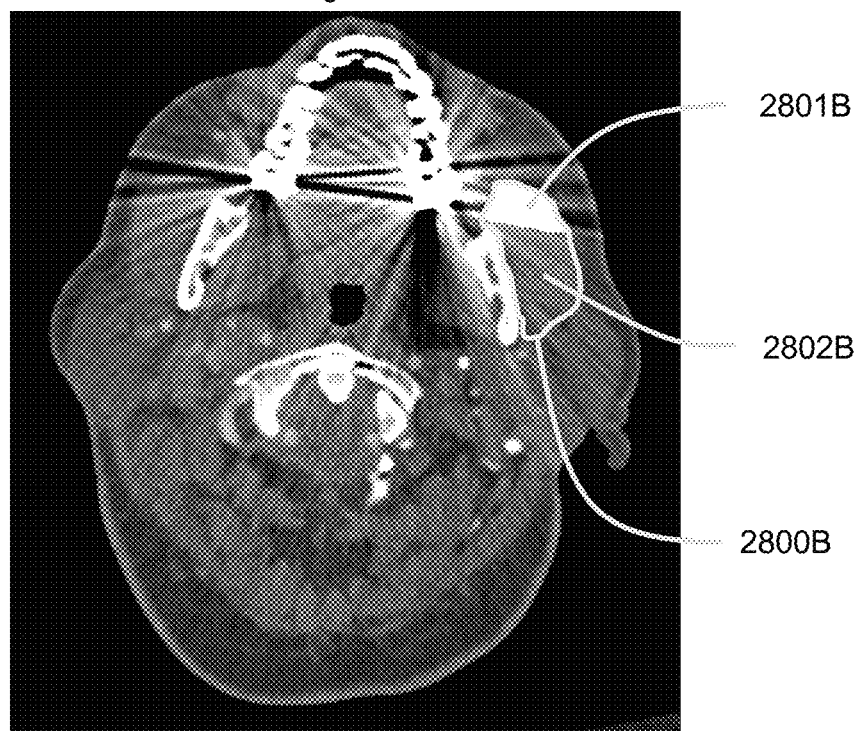
FIG. 28B illustrates generating a customized volume to optimize accuracy of measurement.

FIG. 28B illustrates generating a customized volume to optimize accuracy of measurement. 2800B illustrates segmentation to define the borders of the left masseter muscle. 2801B illustrates an area within the segmented masseter muscle adversely affected by streak artifact by CT, which is eliminated from the analysis. 2802B illustrates an area within the segmented masseter muscle not adversely affected by an imaging artifact, which is included in the analysis. Thus, only portions of the image not adversely affected by imaging artifact are included in the analysis. In this example, the left masseter was divided into two parts (one included for measurement and the other eliminated from measurement). In some embodiments, more than two regions can be included and the shape of the customized volume can be spherical, cube, irregular or other shapes. Also, this process can be performed on a 2D slice as well. In the preferred embodiment, the artifacts are detected by an artificial intelligence (AI algorithm.

Figure 29:
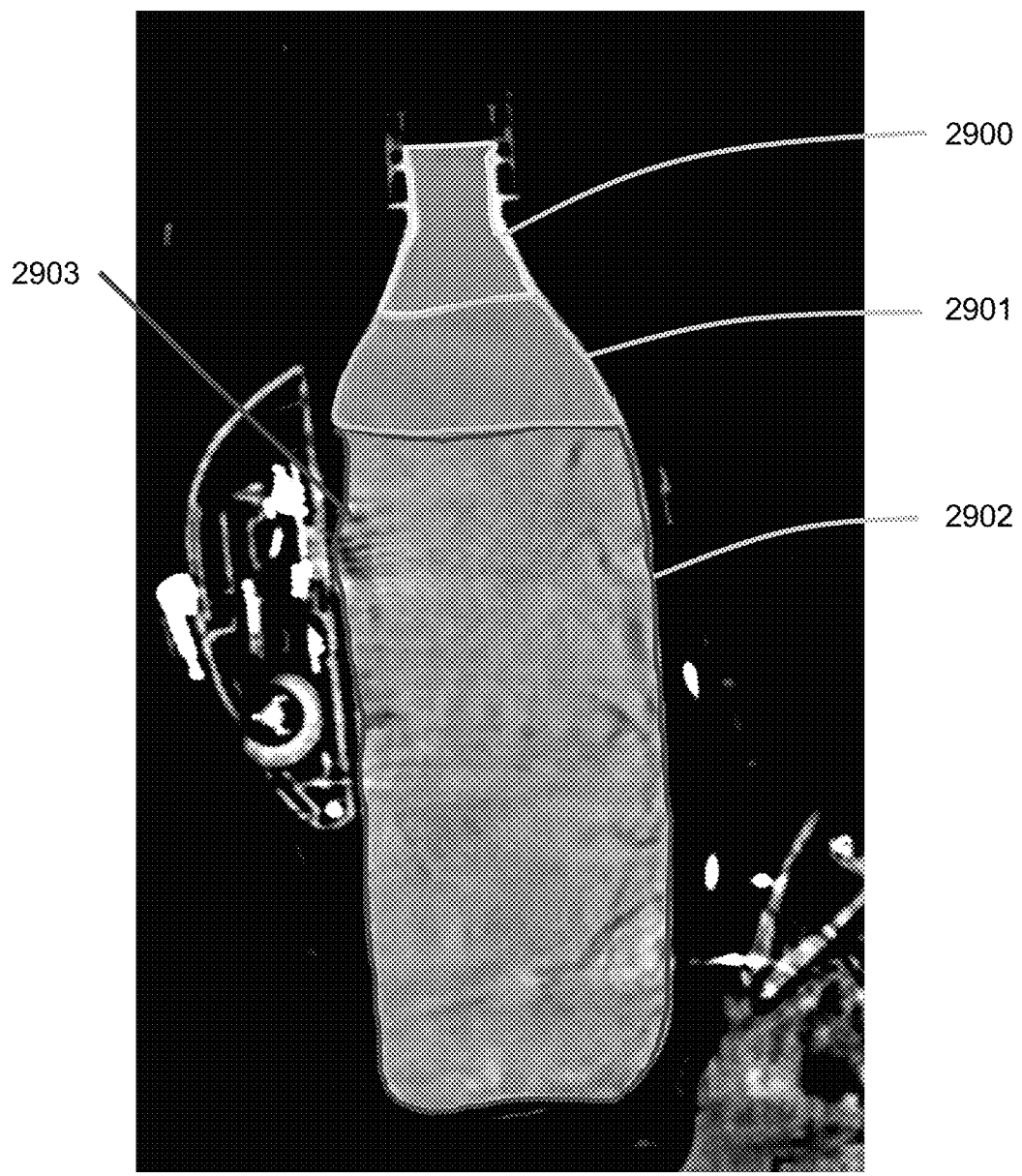
FIG. 29 illustrates generating multiple customized volumes and using weighting factors to optimize accuracy of measurement.

FIG. 29 illustrates generating multiple customized volumes and using weighting factors to optimize accuracy of measurement. In this example, the imaging scan is a CT scan. The object of interest is a bottle. The problem is that there is artifact over some portions of the bottle. The key question is "what is the Hounsfield Units" of the bottle? An accurate measurement is critical for accurate characterization. In this example, the bottle has been segmented into three different sub-volumes. The first sub-volume 2900 has no significant artifact and the measurement accuracy would be highest in this region; however, in some situations it is important to evaluate the whole bottle, not just a portion. The second sub-volume 2901 has some heterogeneous appearance and the measurement in this second sub-volume would be lower than the first sub-volume 2900. The third sub-volume 2902 has streak artifact 2903, which can cause the measurement to be inaccurate. In some embodiments, classification can be performed based on the various regions. For example, the first sub-volume 2900 could be classified as water based on its density, the second sub-volume 2901 could be classified as juice and the third sub-volume could be classified as olive oil. In some embodiments, classification can be performed based on a composite analysis of multiple sub-volumes. For example, the first sub-volume 2900, the second sub-volume 2901 and the third sub-volume 2902 can be classified together as olive oil. The optimum method for performing a composite analysis of multiple sub-volumes is to use weighting factors to determine the most accurate measurement. For example, suppose the volume of a container is 30 mL and there were three sub-volumes of 10 mL each. The first sub-volume of 10 mL was determined to have a Hounsfield Unit measurement of 8. The second sub-volume was determined to have a Hounsfield Unit of 12. The third sub-volume was determined to have a Hounsfield Unit of 20. Equal weighting of each sub-volume would result in (8+12+20)/3 or an overall density of 13.33. However, if the first sub-volume and second sub-volume had little artifact and the third sub-volume had significant artifact, a weighting factor system could be utilized. Assume that the first sub-volume was given a 0.4 weighting factor, the second sub-volume was given a 0.4 weighting factor and the third sub-volume was given a 0.2 weighting factor. Then, this would result in 8*0.4+12*0.4+20*0.2=12. Factors that can be used as weighting factors include, but are not limited to, the following: amount of artifact; sub-volume; standard deviation; and others. In some embodiments, a tilt analysis can be performed to determine: (1) air-fluid levels; and (2) layering within materials. The tilt analysis would include performing a first scan with the object in a first orientation and a second scan with the object in a second orientation wherein the second orientation is different from the first orientation. In some embodiments, a modified segmented region analysis is performed as taught in U.S. patent application Ser. No. 16/785,606, IMPROVING IMAGE PROCESSING VIA A MODIFIED SEGMENTED STRUCTURE, which is incorporated by reference in its entirety. Since the lining of bottles or structures may have a different material property than the fluid enclosed, a modified segmented structure with a conformal (inward direction) could be used to subtract the lining of the bottles to further improve accuracy of measurement of the bottles. In some embodiments, a histogram analysis could be used to eliminate data elements within some ranges, but preserve data elements within other ranges.

Figure 30A:
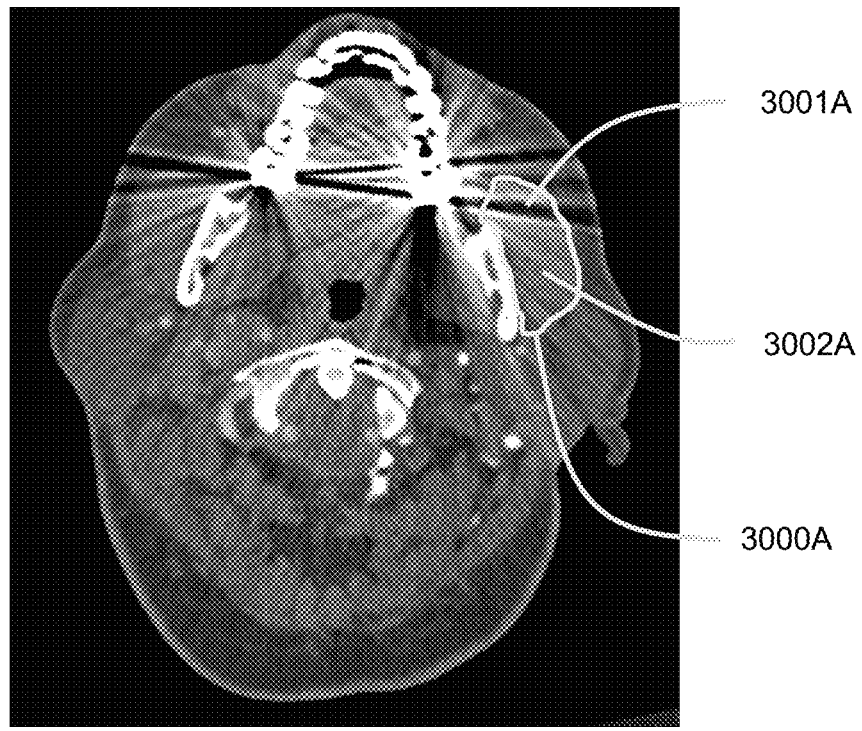
FIG. 30A illustrates an image of an object containing some areas whose data elements are inaccurate due to imaging artifacts and some areas whose data elements are accurate (i.e., not adversely affected by an imaging artifact).

FIG. 30A illustrates an image of an object containing some areas whose data elements are inaccurate due to imaging artifacts and some areas whose data elements are accurate (i.e., not adversely affected by an imaging artifact). 3000A illustrates segmentation to define the borders of the left masseter muscle. 3001A illustrates an area within the segmented masseter muscle adversely affected by streak artifact by CT. 3002A illustrates an area within the segmented masseter muscle not adversely affected by an imaging artifact.

Figure 30B:
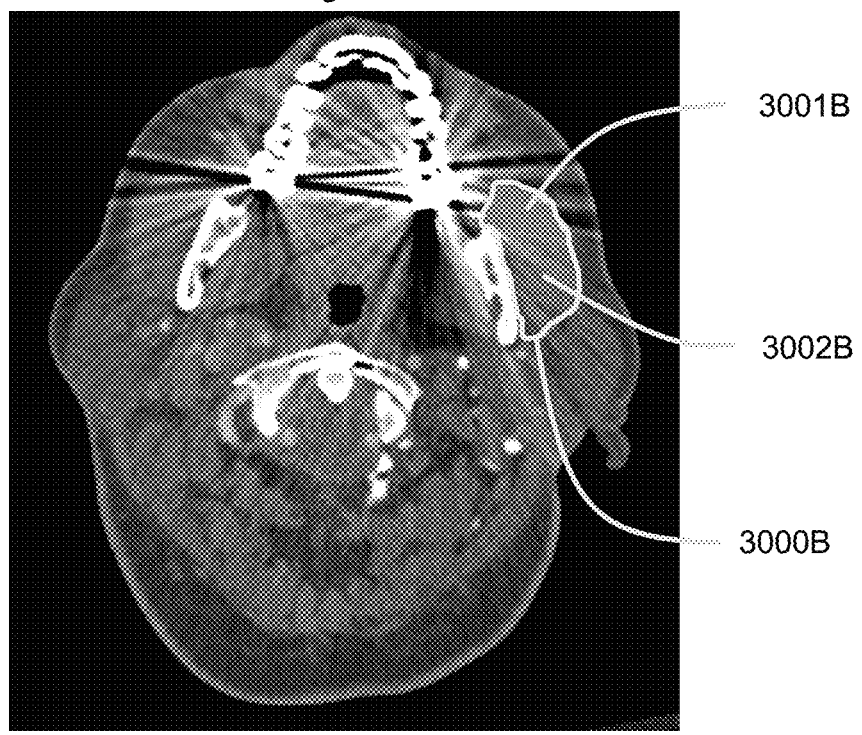
FIG. 30B illustrates a modified image to correct for an imaging artifact.

FIG. 30B illustrates a modified image to correct for an imaging artifact. 3000B illustrates segmentation to define the borders of the left masseter muscle. 3001B illustrates an area within the segmented masseter muscle whose data units are altered by an AI algorithm to get rid of the streak artifact. Some of the white lines of streak artifact (whose Hounsfield Units are erroneously elevated) are altered to lower their Hounsfield Units. Some of the black lines of streak artifact (whose Hounsfield Units are erroneously decreased) are altered to raise their Hounsfield Units. This results in a modified image because some of the data elements (e.g., voxels) have altered data units by an AI algorithm. 3002A illustrates an area within the segmented masseter muscle not adversely affected by an imaging artifact and these areas would not be altered.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method comprising:
    performing an imaging examination of a volume to generate a 3D dataset;
    performing segmentation of an object within said 3D dataset;
    performing an analysis to determine whether said object contains an imaging artifact;
    if said imaging artifact is identified, designing a customized volume to exclude said imaging artifact wherein said customized volume comprises a portion of said object;
    performing a measurement of data units within said customized volume; and
    comparing said measurement of data units with a material classification database wherein said material classification database contains data units associated with a list of known type of materials; and
    classifying a material of said object based on at least said comparing said measurement data units with said material classification database.

2. The method of claim 1 further comprising wherein said imaging examination is a CT scan or an MM scan.

3. The method of claim 1 further comprising wherein said imaging examination is a LIDAR scan.

4. The method of claim 1 further comprising wherein said customized volume is an irregular shape.

5. The method of claim 1 further comprising wherein data units outside of said object are analyzed to characterize said imaging artifact.

6. The method of claim 1 further comprising wherein said performing an analysis to determine whether said object contains said imaging artifact comprises an artificial intelligence algorithm.

7. The method of claim 1 further comprising wherein data unit assurance markers assist in performing an analysis to determine whether said object contains an imaging artifact.

8. A method comprising:
    performing an imaging examination of a volume to generate a 3D dataset;
    performing segmentation of an object within said 3D dataset;
    performing an analysis to determine whether said object contains an imaging artifact;
    if said imaging artifact is identified, performing a correction of said imaging artifact wherein said correction comprises correcting data units of a portion of said object;
    performing a measurement of data units within said object; and
    comparing said measurement of data units with a material classification database wherein said material classification database contains data units associated with a list of known type of materials; and
    classifying a material of said object based on at least said comparing said measurement of data units with said material classification database.

9. The method of claim 8 further comprising wherein said imaging artifact is segmented.

10. The method of claim 8 further comprising wherein data units outside of said object are analyzed to characterize said imaging artifact.

11. The method of claim 8 further comprising wherein said correction of said imaging artifact is performed using an artificial intelligence algorithm to generate a modified dataset.

12. The method of claim 8 further comprising wherein said modified dataset is displayed to said user.

13. The method of claim 8 further comprising wherein data unit assurance markers assist in performing an analysis to determine whether said object contains an imaging artifact.

14. The method of claim 13 further comprising wherein said data unit assurance markers comprise at least one of the group consisting of:
    a phantom;
    a homogeneous structure whose data value is unknown; and
    a heterogeneous structure whose data value is unknown, but predictable.

15. A method comprising:
    performing an imaging examination of a volume to generate a 3D dataset;
    performing segmentation of an object within said 3D dataset;
    performing an analysis of said object wherein a first portion of said object contains an imaging artifact and a second portion of said object does not contain an imaging artifact;
    performing a measurement of data units only within said second portion; and
    comparing said measurement of data units with a material classification database wherein said material classification database contains data units associated with a list of known type of materials; and
    classifying a material of said object based on at least said comparing said measurement oi data units with said material classification database.

16. The method of claim 15 further comprising generating a visible boundary of said second portion.

17. The method of claim 15 further comprising generating a visible boundary of said first portion.

18. The method of claim 15 further comprising performing a second measurement of data units within said first portion.

19. The method of claim 18 further comprising using a first weighting factor for the first portion and a second weighting factor for the second portion to determine a composite measurement of data units.

20. The method of claim 15 further comprising performing an analysis of changes in data units in the gravity-dependent layers of said object.

\* \* \* \* \*